(12) United States Patent
Fabian et al.

(10) Patent No.: US 8,674,089 B2
(45) Date of Patent: Mar. 18, 2014

(54) MICHAEL ADDITION REACTION PRODUCT AND ACTIVE ENERGY RAY-CURABLE COMPOSITION

(75) Inventors: Kutzner Fabian, Berlin (DE); Gaudl Kai-uwe, Hohen Neuendorf (DE); Yoshinobu Sakurai, Sakura (JP); Tatsushi Okuda, Sakura (JP)

(73) Assignee: DIC Corporation, Tokyo (JP)

( * ) Notice: Subject to any disclaimer, the term of this patent is extended or adjusted under 35 U.S.C. 154(b) by 54 days.

(21) Appl. No.: 13/379,781

(22) PCT Filed: Jun. 28, 2010

(86) PCT No.: PCT/JP2010/060952
§ 371 (c)(1),
(2), (4) Date: Apr. 10, 2012

(87) PCT Pub. No.: WO2011/001928
PCT Pub. Date: Jan. 6, 2011

(65) Prior Publication Data
US 2012/0190846 A1    Jul. 26, 2012

(30) Foreign Application Priority Data
Jun. 29, 2009  (JP) ................. 2009-153604

(51) Int. Cl.
*C07D 403/10* (2006.01)
*C07D 295/155* (2006.01)
*C07D 295/15* (2006.01)

(52) U.S. Cl.
USPC ............ 540/575; 544/357; 544/394; 544/158

(58) Field of Classification Search
USPC ............................ 540/575; 544/357, 394, 158
See application file for complete search history.

(56) References Cited

U.S. PATENT DOCUMENTS

| 4,987,160 A | 1/1991 | Frihart et al. |
| 4,987,210 A | 1/1991 | Login et al. |
| 5,487,339 A | 1/1996 | Breventani et al. |
| 2008/0045620 A1 | 2/2008 | Herlihy et al. |

FOREIGN PATENT DOCUMENTS

| JP | 2-269123 A | 11/1990 | |
| JP | 10-512856 A | 12/1998 | |
| JP | 2005-505615 A | 2/2005 | |
| JP | 2007-534800 A | 11/2007 | |
| JP | 2008-519760 | * 6/2008 | ........... C07D 295/10 |
| JP | 2008-519760 A | 6/2008 | |
| JP | 2008-523205 A | 7/2008 | |
| WO | 2007/043431 A1 | 4/2007 | |

OTHER PUBLICATIONS

Notification of Reason for Refusal dated May 12, 2011, issued in corresponding Japanese Patent Application No. 2010-537200.
International Search Report of PCT/JP2010/060952, mailing date Aug. 10, 2010.

* cited by examiner

*Primary Examiner* — Kristin Vajda
(74) *Attorney, Agent, or Firm* — Westerman, Hattori, Daniels & Adrian, LLP

(57) ABSTRACT

The present invention provides a Michael addition reaction product between a specified compound having a group which functions as a Michael donor and a monomer or polymer having a group which functions as a Michael acceptor, a photoinitiator containing the Michael addition reaction product, and an active energy ray-curable composition containing the photoinitiator. The compound having a group functioning as a Michael donor used in the present invention is a phenyl ketone derivative and is characterized by having an amino group or a mercapto group as the group functioning as a Michael donor.

16 Claims, No Drawings

MICHAEL ADDITION REACTION PRODUCT AND ACTIVE ENERGY RAY-CURABLE COMPOSITION

TECHNICAL FIELD

The present invention relates to a compound having a group that functions as a Michael donor, a Michael addition reaction product obtained from the compound, a photoinitiator containing the Michael addition reaction product, an active energy ray-curable composition containing the photoinitiator, an active energy ray ink composition, and an active energy ray-curable surface coating composition.

BACKGROUND ART

From the viewpoint of high production efficiency, reduction in cost of curing energy, and VOC reduction, active energy ray-curing systems have been widely used. In particular, an ultraviolet curing system becomes a main stream because of its lower introduction cost and smaller installation area of equipment than other active energy ray curing systems. In the ultraviolet curing system, a photoinitiator is an essential component for starting curing, but the photoinitiator or a decomposition product thereof remains as a low-molecular-weight component in a coating film after curing because the photoinitiator is generally a low-molecular-weight compound. Such a low-molecular-weight component causes an odor of a coating film and an eluted material from the coating film. In particular, in application to ultraviolet curable inks used for printed matters for food packaging, it is strongly demanded to improve migration in which the remaining photoinitiator eluted from a cured product migrates to the back side of a printed matter in direct contact with a food.

For example, Patent Literature 1 discloses an oligomer-type photoinitiator having a plurality of initiator groups in its molecule. A method disclosed in this literature has the effect of decreasing an odor and migration by oligomerizing a photoinitiator, but migration cannot be completely suppressed.

In addition, Patent Literatures 2 and 3 each disclose an ultraviolet ray-durable resin produced by Michael addition reaction between a polyfunctional acrylate and a photoinitiator containing a β-dicarbonyl group. A method disclosed in these literatures is capable of significantly decreasing elusion of a photoinitiator from a cured film by introducing a reactive group in a photoinitiator group and immobilizing the photoinitiator group in the cured film. However, the method exhibits insufficient curing performance and thus has the problem of causing defective curing in application in which a curing rate is required, particularly application to ultraviolet ray-curable inks.

CITATION LIST

Patent Literature

PTL 1: Japanese Unexamined Patent Application Publication (Translation of PCT Application) No. 2005-505615
PTL 2: Japanese Unexamined Patent Application Publication (Translation of PCT Application) No. 2008-523205
PTL 3: Japanese Unexamined Patent Application Publication (Translation of PCT Application) No. 2007-534800

SUMMARY OF INVENTION

Technical Problem

As described above, particularly, in application to ultraviolet ray-curable inks used for printed matters for food packaging, it is strongly demanded to improve migration in which the remaining photoinitiator eluted from a cured product migrates to the back side of a printed matter in direct contact with a food. However, application to UV-curable inks required to have a curing rate has the problem of causing defective curing because of the unsatisfactory effect of suppressing migration or unsatisfactory curing performance in spite of the migration suppressing effect of a photoinitiator.

Accordingly, in consideration of the above-mentioned related art, a problem of the present invention is to provide a Michael addition reaction product between a compound having a group that functions as a Michael donor and a monomer or polymer having a group that functions as a Michael acceptor, the reaction product having a photoinitiator function and excellent curability and suppressing migration, and also provide a photoinitiator containing the Michael addition reaction product, an active energy ray-curable composition containing the photoinitiator, an active energy ray-curable ink composition, and an active energy ray-curable surface coating composition.

Solution to Problem

The present invention has been achieved as a result of repeated intensive researches for resolving the problem and provides a Michael addition reaction product produced by a Michael addition reaction between a compound having a specified group which functions as a Michael donor, and a monomer or polymer having a group which functions as a Michael acceptor.

Further, the present invention provides an active energy ray-curable composition containing the Michael addition reaction product, an active energy ray-curable ink composition, and an active energy ray-curable surface coating composition.

Advantageous Effects of Invention

According to the present invention, it is possible to provide a photoinitiator which suppresses migration and which has excellent curability, an active energy ray-curable composition containing the photoinitiator, an active energy ray-curable ink composition, and an active energy ray-curable surface coating composition.

DESCRIPTION OF EMBODIMENTS

A compound (referred to as a "phenyl ketone derivative" hereinafter) containing a group which functions as a Michael donor used in the present invention is a phenyl ketone derivative, and is characterized by containing an amino group or a mercapto group as the group functioning as a Michael donor. The phenyl ketone derivative containing an amino group or a mercapto group is not particularly limited as long as it contains an amino group or a mercapto group as the group functioning as a Michael donor. Examples thereof include compounds each having a group functioning as a Michael donor, in which a structure of an acetophenone-based, benzoin ether-based, benzyldimethyl ketal-based, benzophenone-based, thioxanthone-based, α-acyloxime-based, acylphosphine oxide-based, coumarin-based, anthraquinone-based, or titanocene-based photoinitiator is substituted by one or two secondary amino groups, such as piperazinyl groups, methylamino groups, ethylamino groups, or benzylamino groups, or mercapto groups.

Examples of such compounds include compounds represented by the following formulae (1) to (8):

[Chem. 1]

(1)
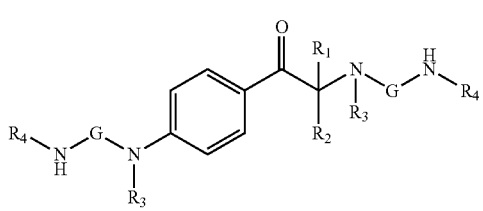

(2)
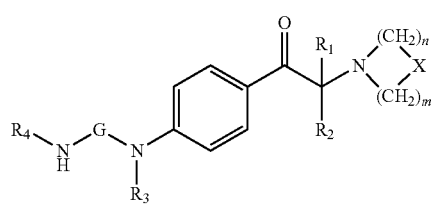

(3)
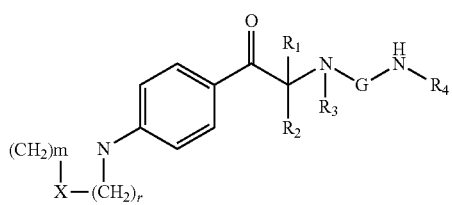

(4)
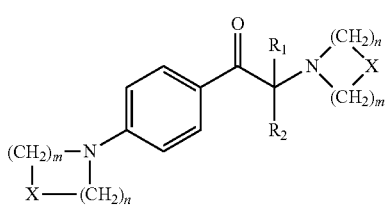

(5)
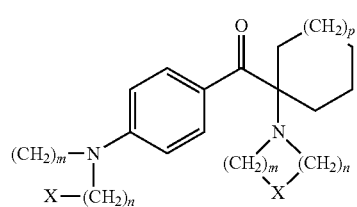

(6)
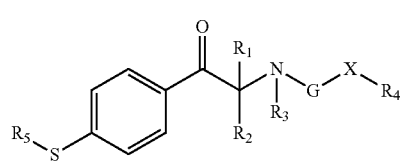

(7)
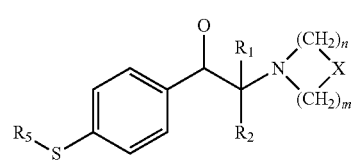

(8)
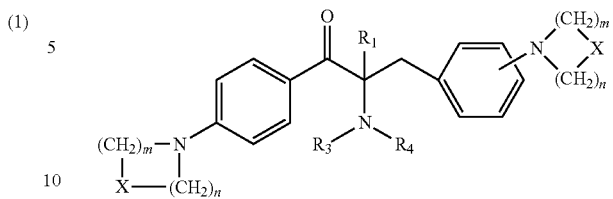

(In the formulae, $R_1$ and $R_2$ each independently represent an alkyl group having 1 to 12 carbon atoms, an allyl group, a cycloalkyl group, an aryl group, or an aralkyl group, G represents an alkylene group having 1 to 12 carbon atoms, a divalent aryl group, or a divalent aralkyl group, X represents NH or O, $R_3$ and $R_4$ each independently represent an alkyl group having 1 to 12 carbon atoms, $R_5$ represents a hydrogen atom, an alkyl group having 1 to 12 carbon atoms, a cycloalkyl group, an aryl group, or an aralkyl group, or a thioalkyl group having 2 to 12 carbon atoms, m and n each represent 2 or 3, and p represents 0, 1, 2, or 3.)

Specific examples include compounds of formulae (9) to (42) described below. Among these compounds, aminoalkylphenone-based initiators (9) to (19), (23), (29) to (33), and (36) to (42) each containing one or two secondary amino groups, such as piperazinyl groups, or mercapto groups are preferred, and (9) to (19) are particularly preferred.

[Chem. 2]

(9)
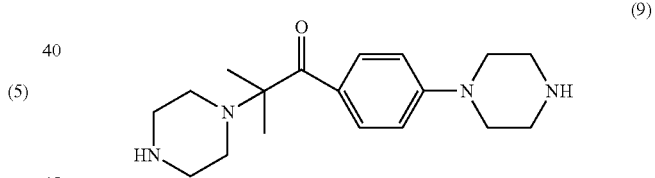

(10)
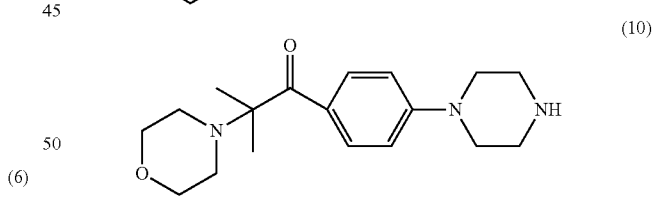

(11)
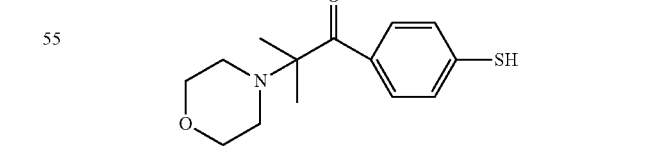

(12)
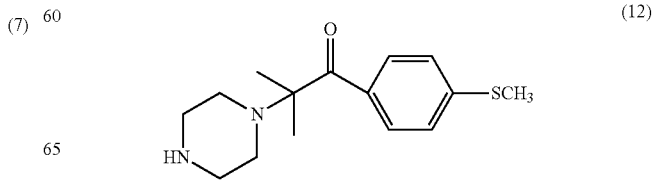

(13) 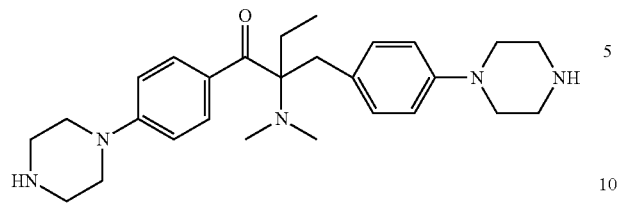
(14) 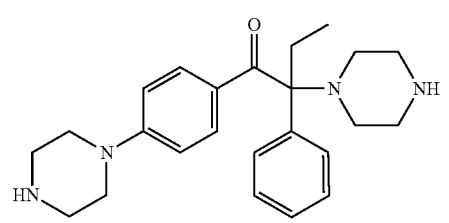
(15) 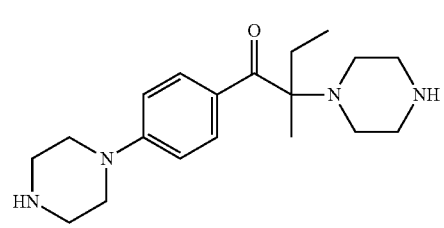
(16) 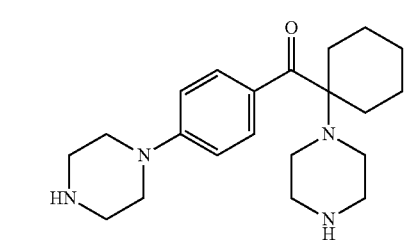
(17) 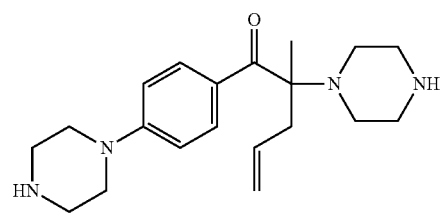
(18) 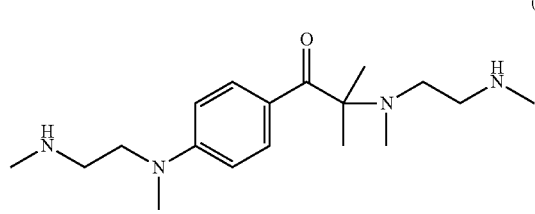
(19) 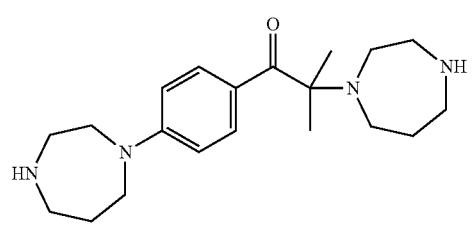
[Chem. 3]
(20) 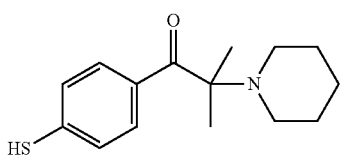
(21) 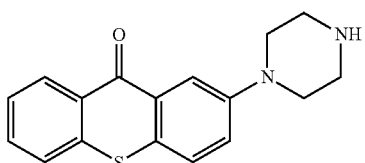
(22) 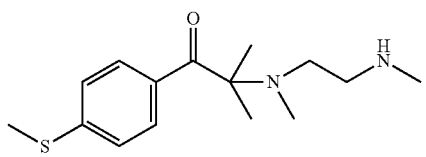
(23) 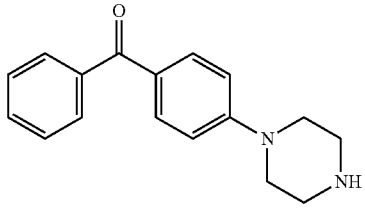
(24) 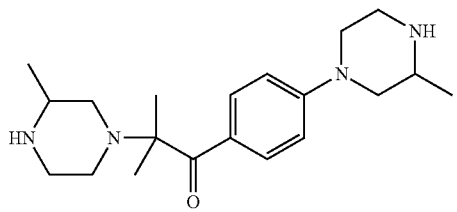
(25) 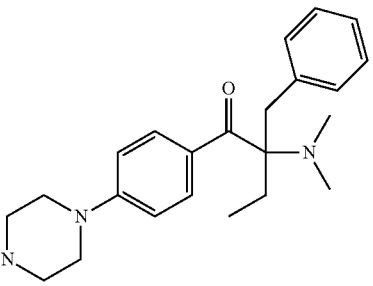
(26) 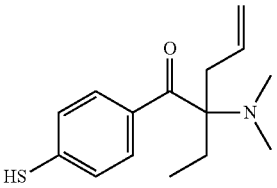

[Chem. 4]
(27) 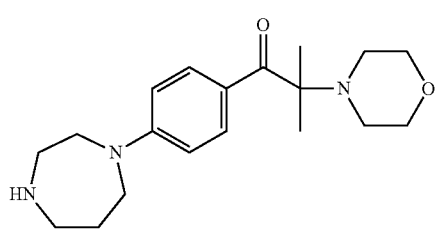
(28) 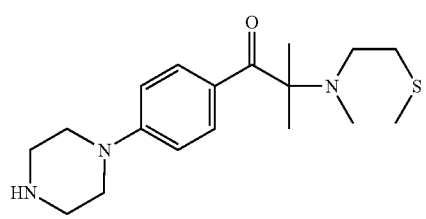
(29) 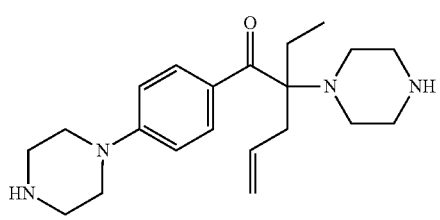
(30) 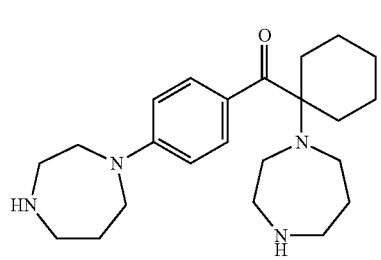
(31) 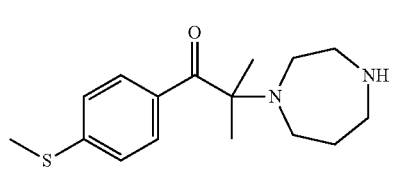
(32) 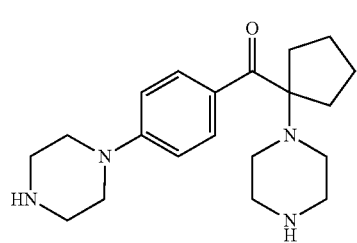
(33) 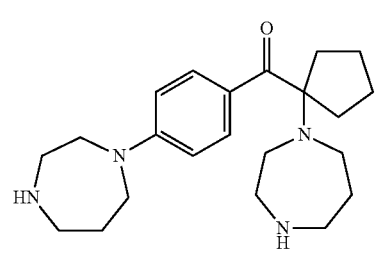
(34) 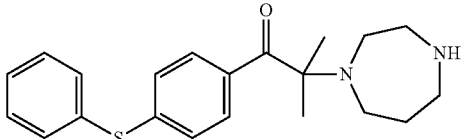
(35) 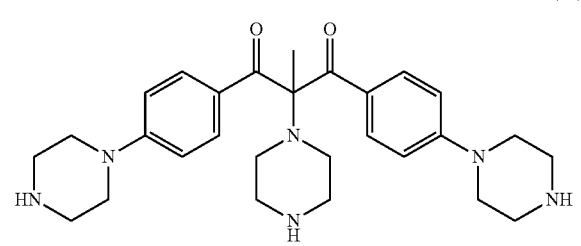
(36) 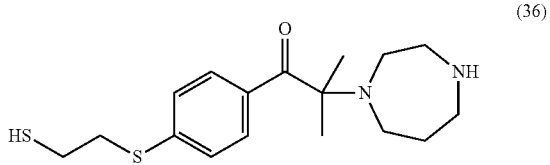
(37) 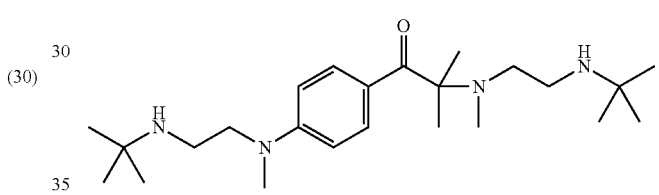
(38) 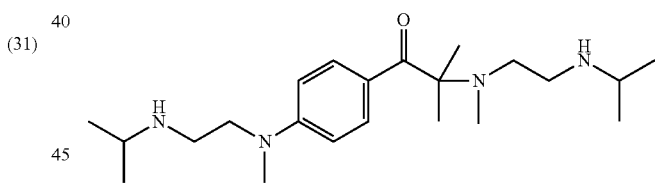
(39) 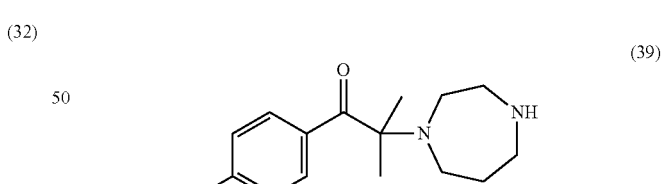
(40) 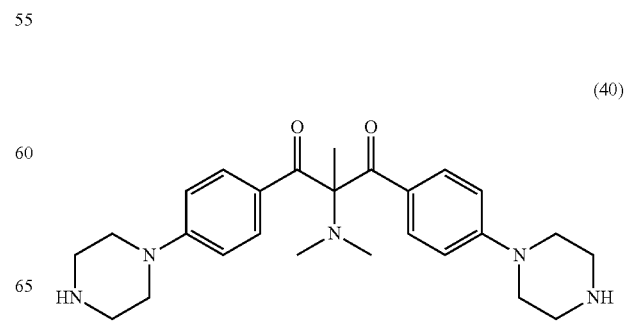

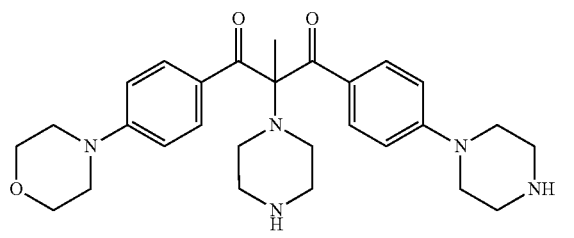

(41)

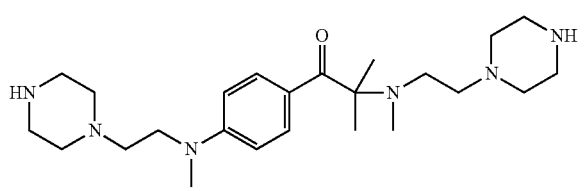

(42)

These phenyl ketone derivatives can be produced by, for example, a known common reaction of halogenated benzene with sodium sulfide or a secondary amino compound, such as morpholine, piperidine, N-methylpiperazine, N,N'-dimethylethylenediamine, N,N'-diethylethylenediamine, N—N'-dimethylpropylenediamine, piperazine, or 2-methylpiperazine.

Taking the compound represented by formula (9) for example, the compound can be produced according to the following formula (44).

[Chem. 5]

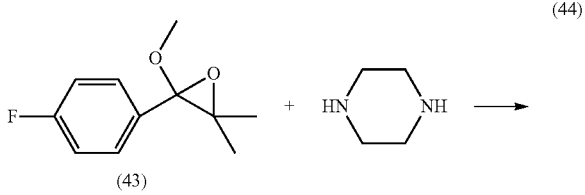

(44)

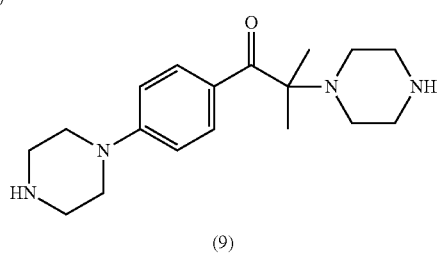

(9)

That is, the epoxy group-containing halogenated benzene (43) may be reacted with piperazine.

The reaction can be performed at 20° C. to 200° C., but a preferred reaction temperature is, for example, 100° C. to 160° C. An organic solvent may be or may not be used as a reaction solvent. When the organic solvent is used, the solvent is not particularly limited as long as it has a boiling point of 100° C. or more and produces no side reaction, but aromatic hydrocarbon solvents such as toluene, xylene, and the like, and ether solvents such as diethylene glycol dimethyl ether, diethylene glycol diethyl ether, and the like can be used.

The reaction time is 1 to 40 hours, and the reaction is generally performed for 10 to 20 hours.

Also the other phenyl ketone derivatives of the formulae (10) to (42) can be properly produced by the same method.

The phenyl ketone derivatives of the present invention each function as a group functioning as a Michael donor and are involved in a Michael addition reaction with a monomer or polymer having a group functioning as a Michael acceptor. The monomer or polymer having a group functioning as a Michael acceptor is not particularly limited as long as it is involved in the Michael addition reaction, and α,β-unsaturated carbonyl compounds such as maleimide derivatives, maleate derivatives, fumarate derivatives, (meth)acrylate derivatives, and the like can be used. In particular, the (meth)acrylate derivatives are preferred.

Examples of the (meth)acrylates include, but are not limited to, monofunctional acrylates such as ethyl(meth)acrylate, butyl(meth)acrylate, and the like;

difunctional (meth)acrylates such as diethylene glycol di(meth)acrylate, tripropylene glycol di(meth)acrylate, hexanediol di(meth)acrylate, neopentyl glycol di(meth)acrylate, and the like;

polyfunctional (meth)acrylates such as trimethylolpropane tri(meth)acrylate and an ethylene oxide-modified product thereof, pentaerythritol tri or tetra(meth)acrylate and an ethylene oxide-modified product thereof, ditrimethylolpropane tetra(meth)acrylate and an ethylene oxide-modified product thereof, dipentaerythritol tetra, penta, or hexa(meth)acrylate and a caprolactone-modified product thereof, and the like;

epoxy(meth)acrylates produced by a reaction between (meth)acrylic acid and polyglycidyl ether such as bisphenol A diglycidyl ether, trimethylolpropane triglycidyl ether, or the like;

urethane(meth)acrylates produced by a reaction between a polyisocyanate compound such as a isophorone diisocyanate or hexamethylene diisocyanate trimer and a hydroxyl group-containing acrylate such as hydroxyethyl(meth)acrylate or pentaerythritol tri(meth)acrylate;

polyester(meth)acrylates produced by a reaction between a polybasic acid such as trimellitic acid or succinic acid, polyol such as ethylene glycol or neopentyl glycol, and a hydroxyl group-containing (meth)acrylate such as hydroxyethyl(meth)acrylate or pentaerythritol tri(meth)acrylate; and high-molecular-weight poly(meth)acrylates produced by a reaction between (meth)acrylic acid and a polymer of glycidyl(meth)acrylate and a monofunctional (meth)acrylate. In particular, trifunctional or higher functional (meth)acrylates can be preferably used because Michael addition reaction products which cause little extracts from cured coating films are produced. In addition, these acrylates can be used alone or as a mixture.

The Michael addition reaction between the phenyl ketone derivative having a group which functions as a Michael donor and the monomer or polymer having a group which functions as a Michael acceptor according to the present invention is not particularly limited and can be performed under known common reaction conditions. As a general method, the phenyl ketone derivative containing a group which functions as a Michael donor and the monomer or polymer containing a group which functions as a Michael acceptor may be mixed at 0 to 150° C. in a reaction vessel, and a catalyst and a solvent can also be used.

Examples of the catalyst which can be used include tetraethylammonium fluoride, tetrabutylammonium hydroxide, potassium hydroxide, tetramethylguanidine, diazabicycloundecene, sodium tert-butyrate, tri-n-octylphosphine, triphenylphosphine, and the like.

Examples of the organic solvent include saturated hydrocarbons such as pentane, hexane, heptane, cyclohexane, and the like; aromatic hydrocarbons such as toluene, xylene, and the like; alcohols such as methanol, ethanol, isopropanol, 2-butanol, tert-butanol, ethylene glycol, carbitol, and the like; ethers such as dimethyl ether, diethyl ether, 1,4-dioxane, tetrahydrofuran (THF), and the like; amides such as dimethylformamide (DMF) and the like; halogenated solvents such as chloroform, dichloromethane, and the like; and dimethylsulfoxide (DMSO).

The mixing ratio between the phenyl ketone derivative containing a group which functions as a Michael donor and the monomer or polymer containing a group which functions as a Michael acceptor is not particularly limited, but the number of groups functioning as a Michael acceptor to the number of groups functioning as a Michael donor is preferably 1/30 to 1/1.5. At a ratio exceeding 1/1.5, the initiator tends to be easily eluted from a coating film, while at a ratio of less than 1/30, the curing performance of the Michael addition reaction product tends to be degraded. From the viewpoint of the curing performance of the resultant Michael addition reaction product and the amount of material eluted from a coating film, the ratio is particularly preferably 1/20 to 1/2.

Examples of the Michael addition reaction product obtained as described above include, but are not limited to, compounds of the following formulae (45) to (66):

[Chem. 6]

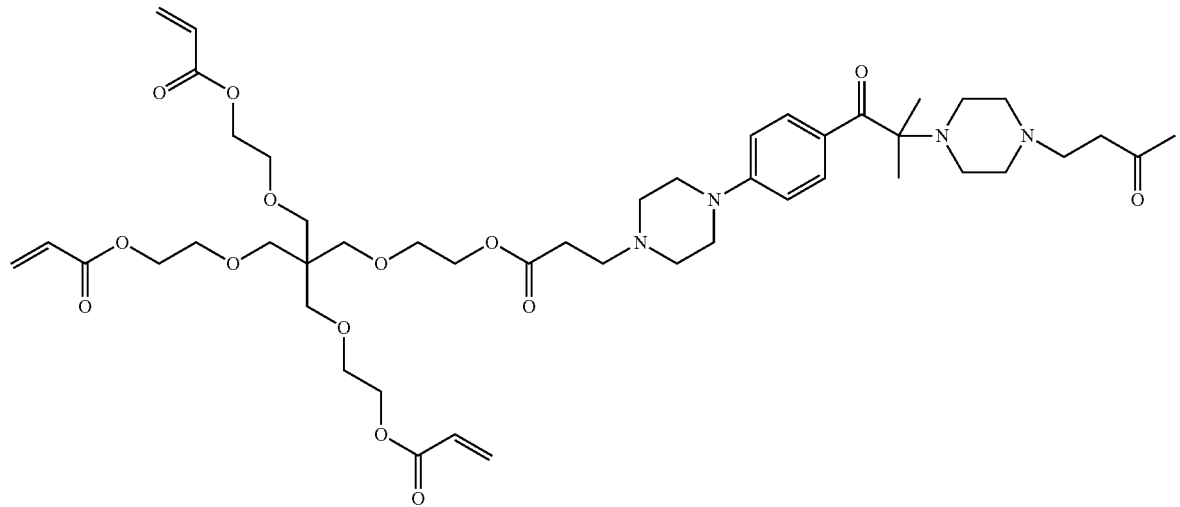

(45)

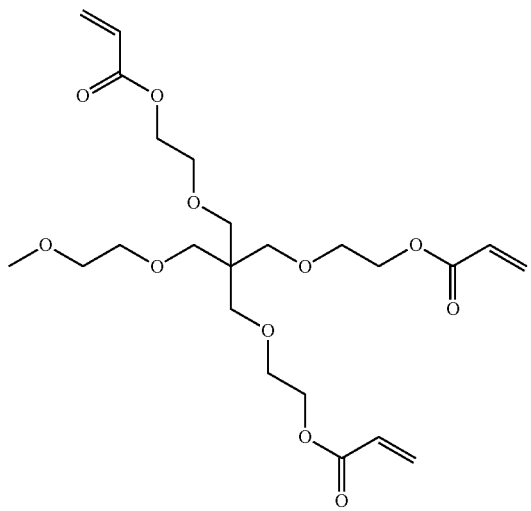

-continued
[Chem. 7]
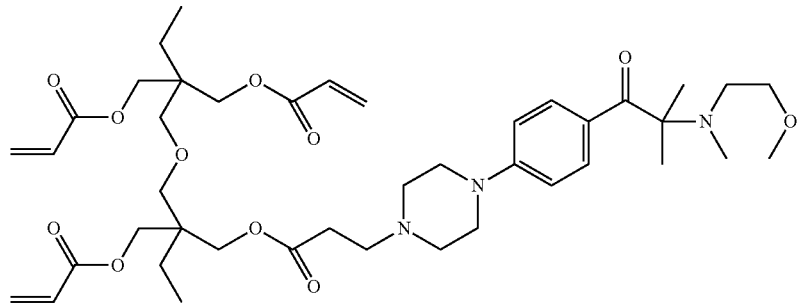
(46)
[Chem. 8]
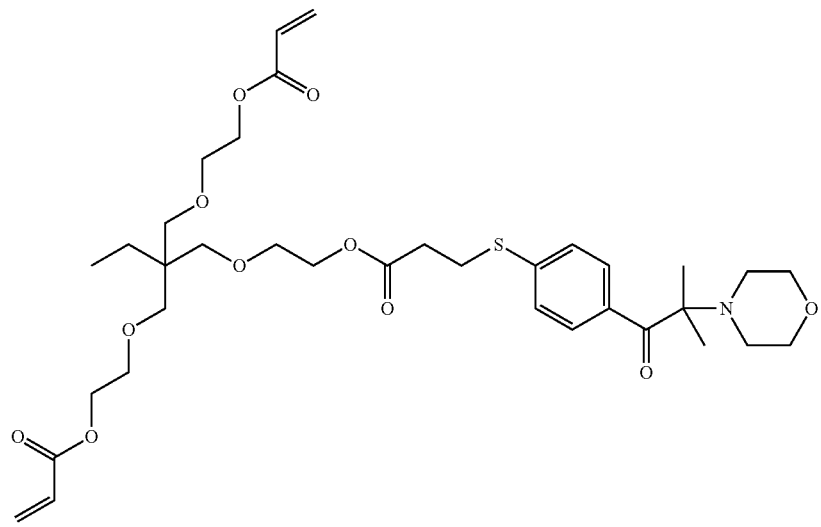
(47)
[Chem. 9]
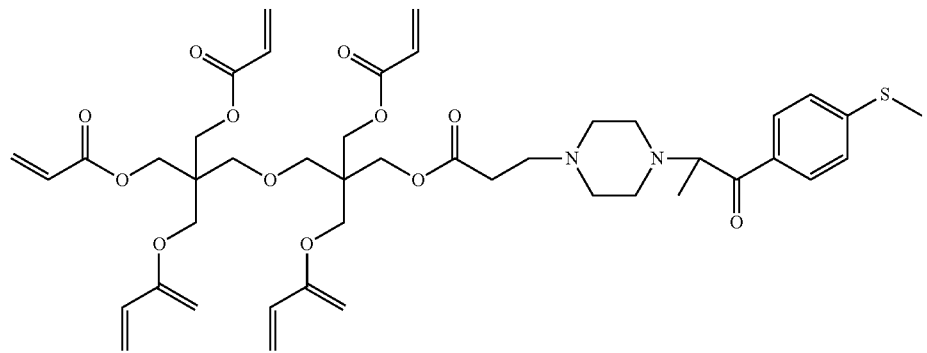
(48)

-continued
[Chem. 10]
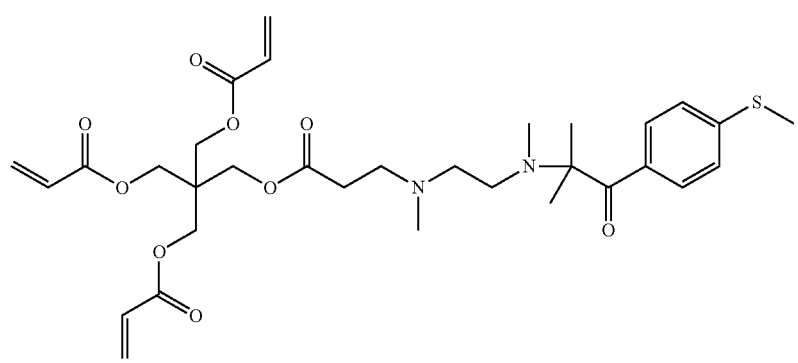
(49)
[Chem. 11]
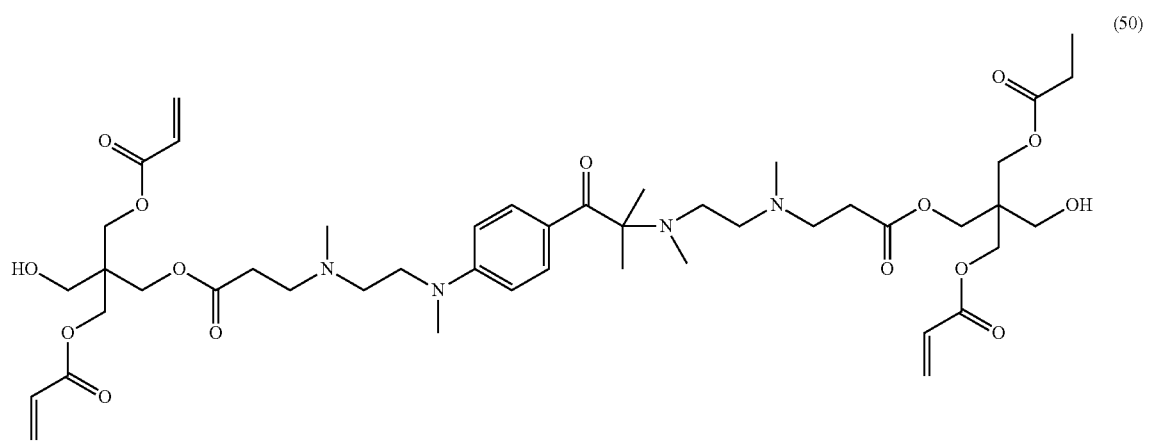
(50)
[Chem. 12]
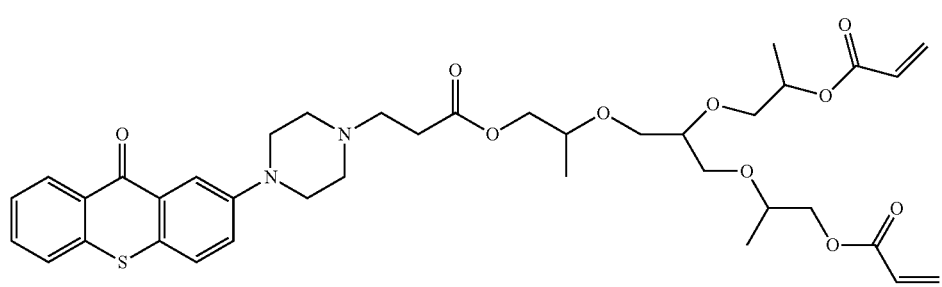
(51)
[Chem. 13]
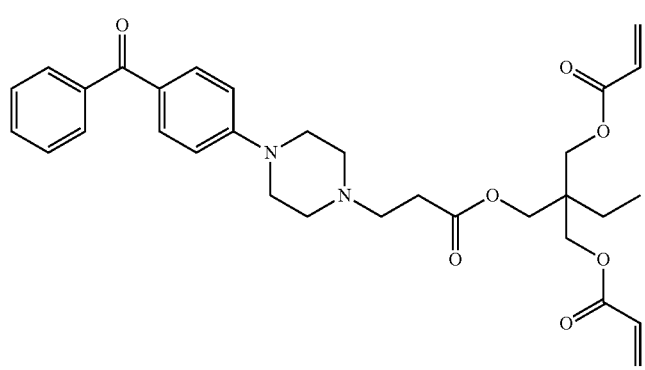
(52)

-continued
[Chem. 14]
(53)
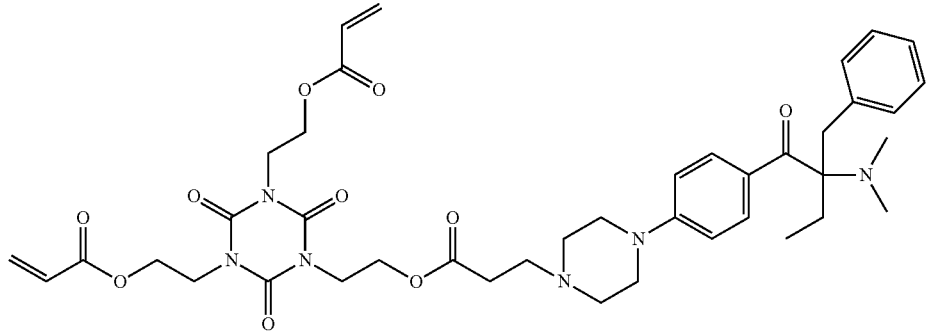
[Chem. 15]
(54)
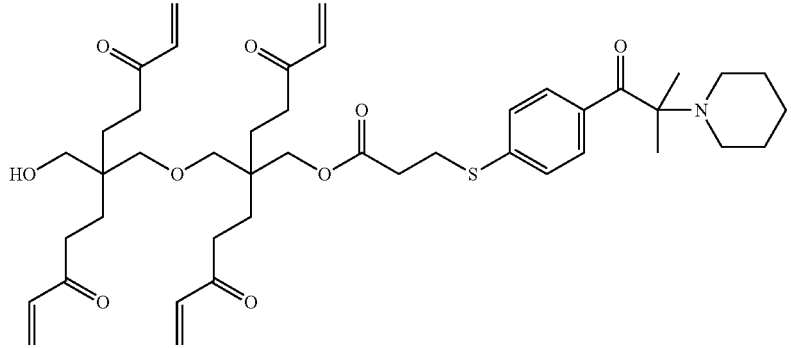
[Chem. 16]
(55)
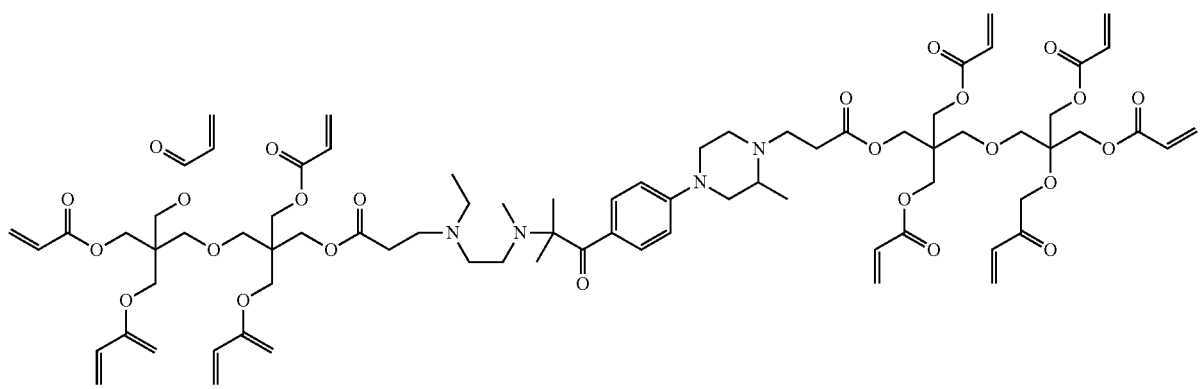
[Chem. 17]
(56)
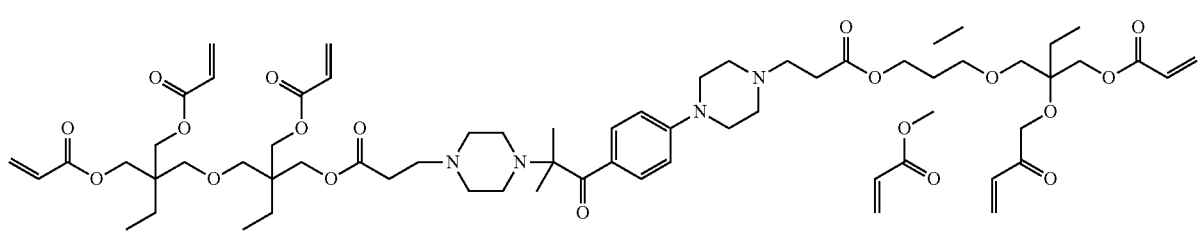

-continued
[Chem. 18] (57)
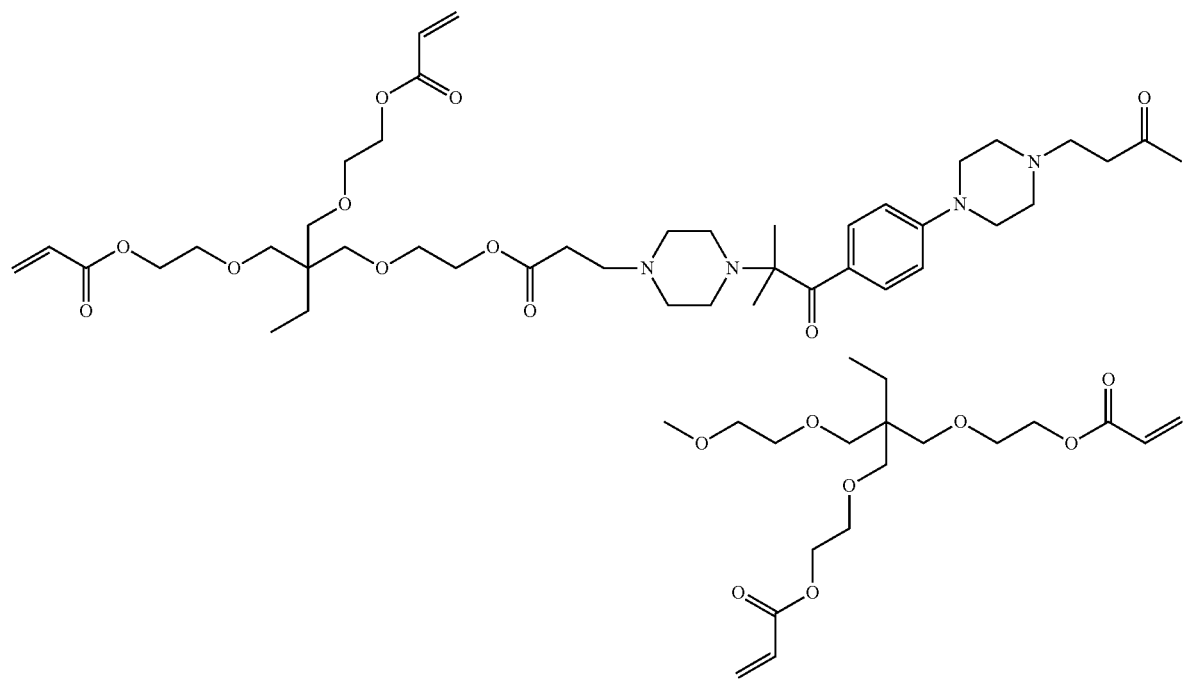
[Chem. 19] (58)
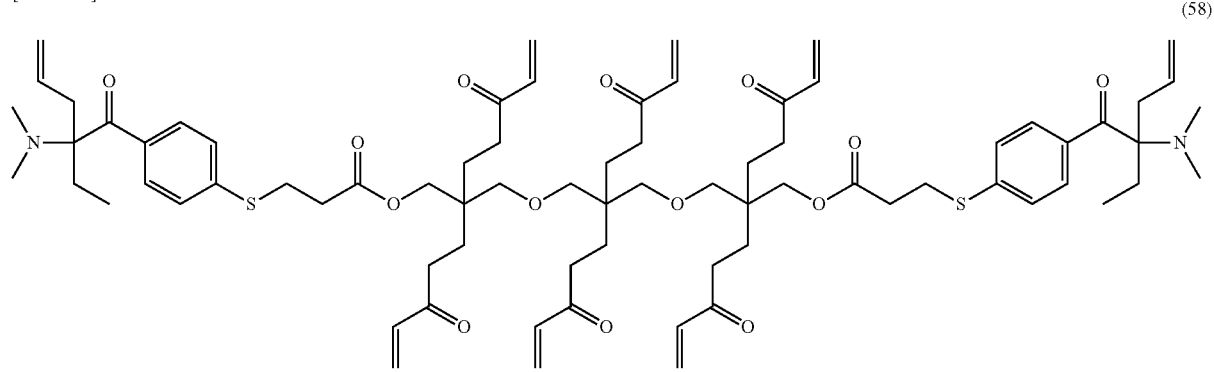
[Chem. 20] (59)
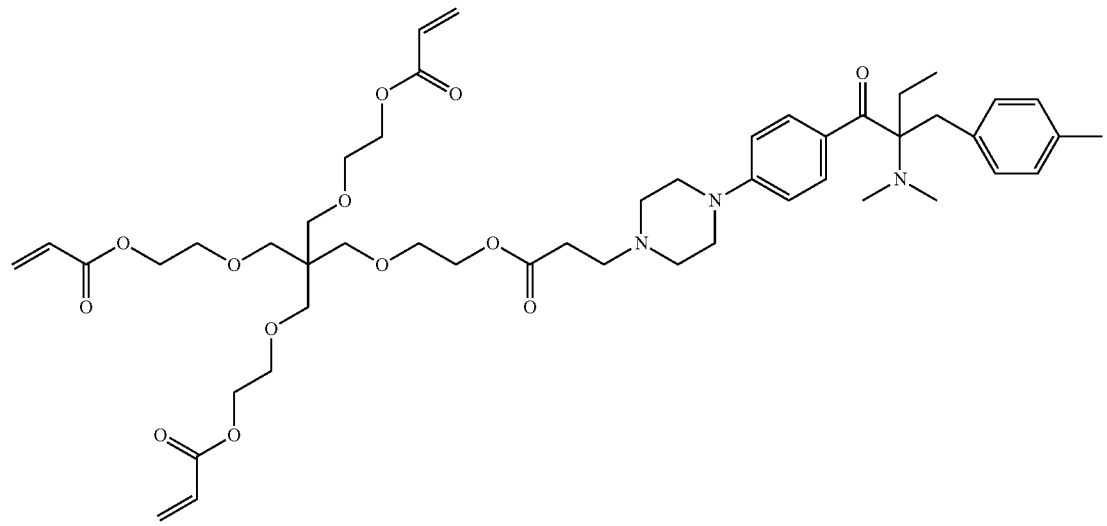

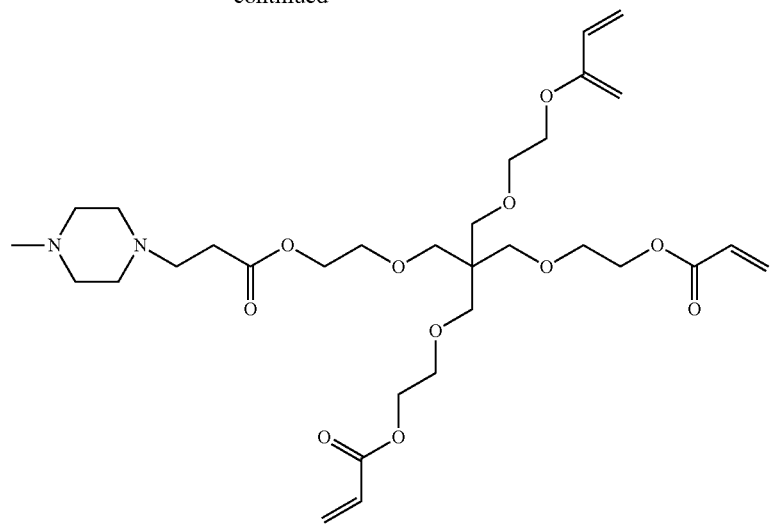
[Chem. 21]
(60)
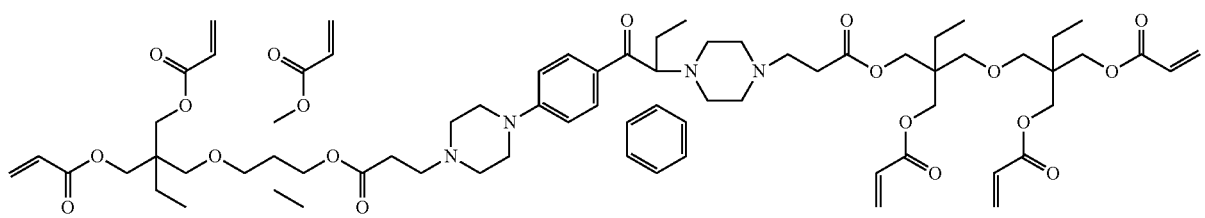
[Chem. 22]
(61)
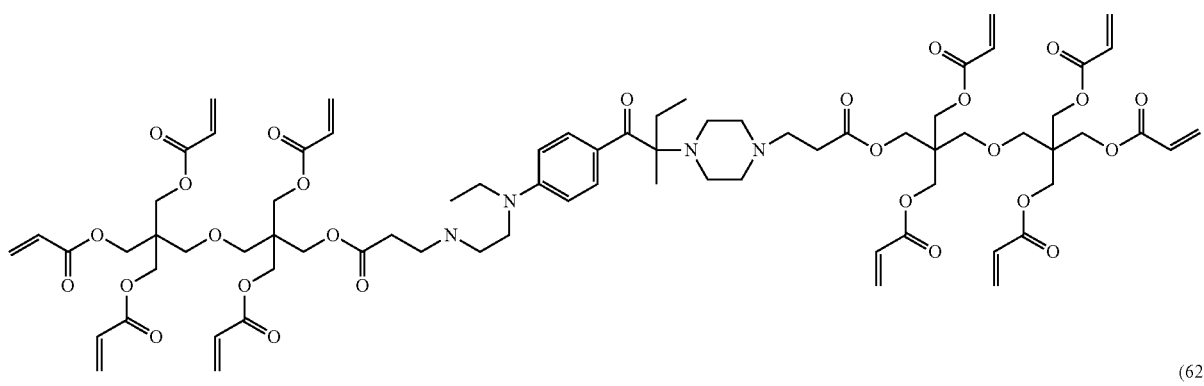
[Chem. 23]
(62)
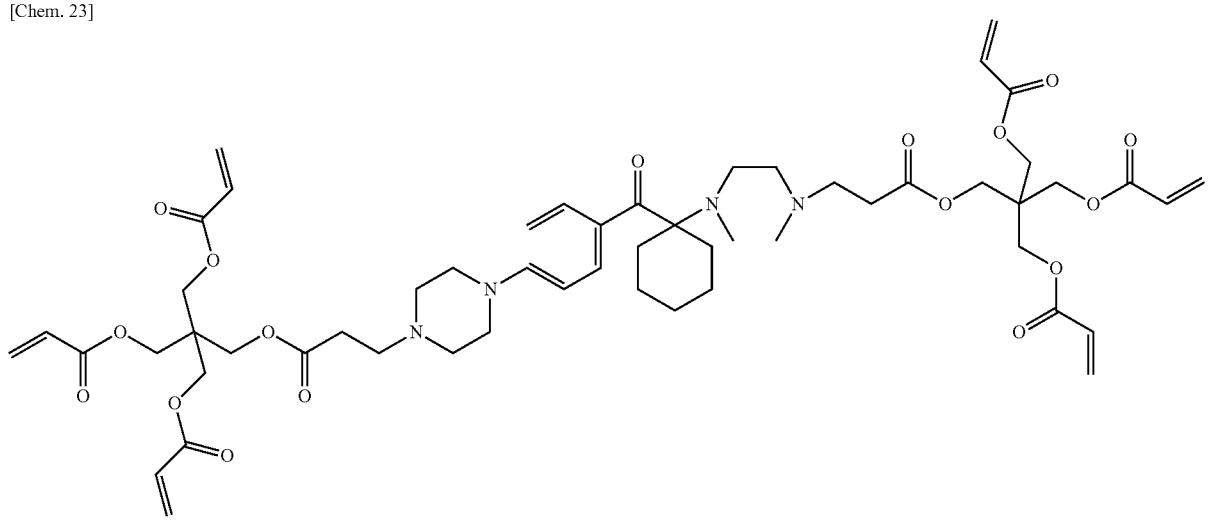

-continued
[Chem. 24]
(63)
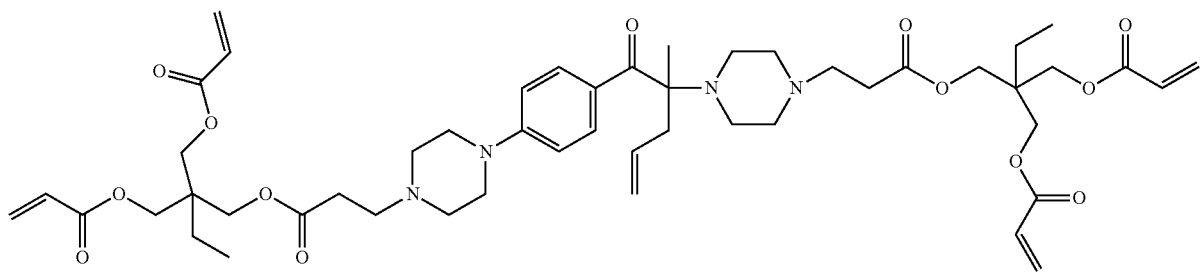
[Chem. 25]
(64)
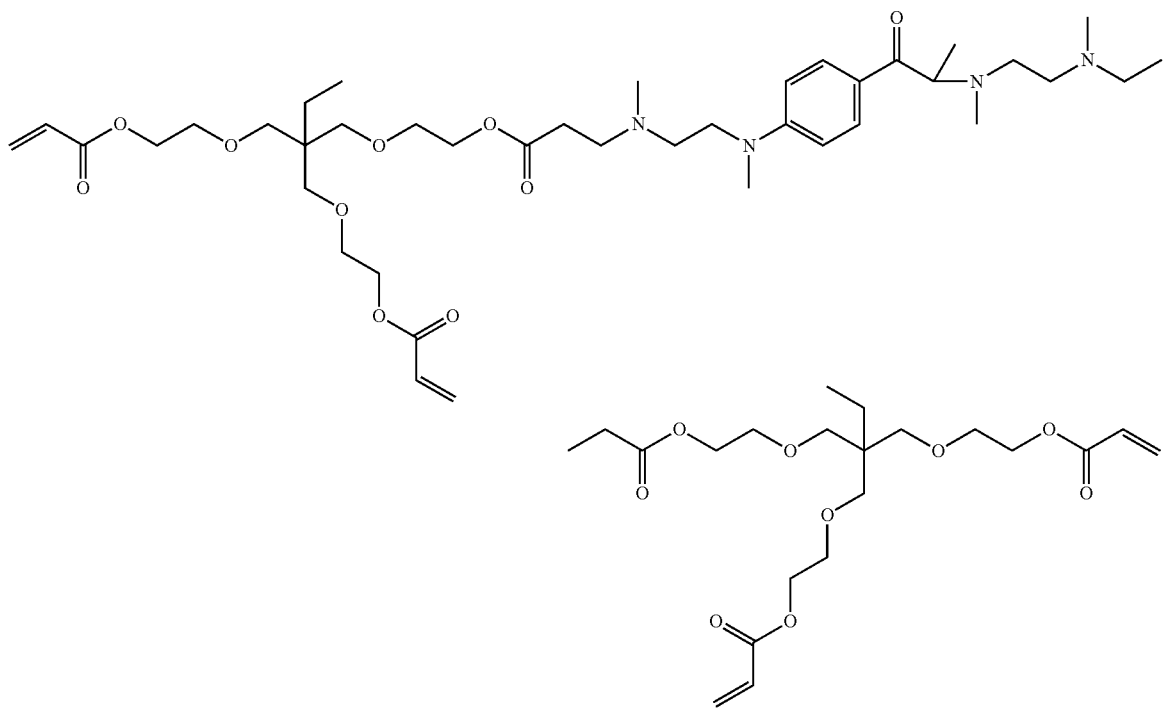
[Chem. 26]
(65)
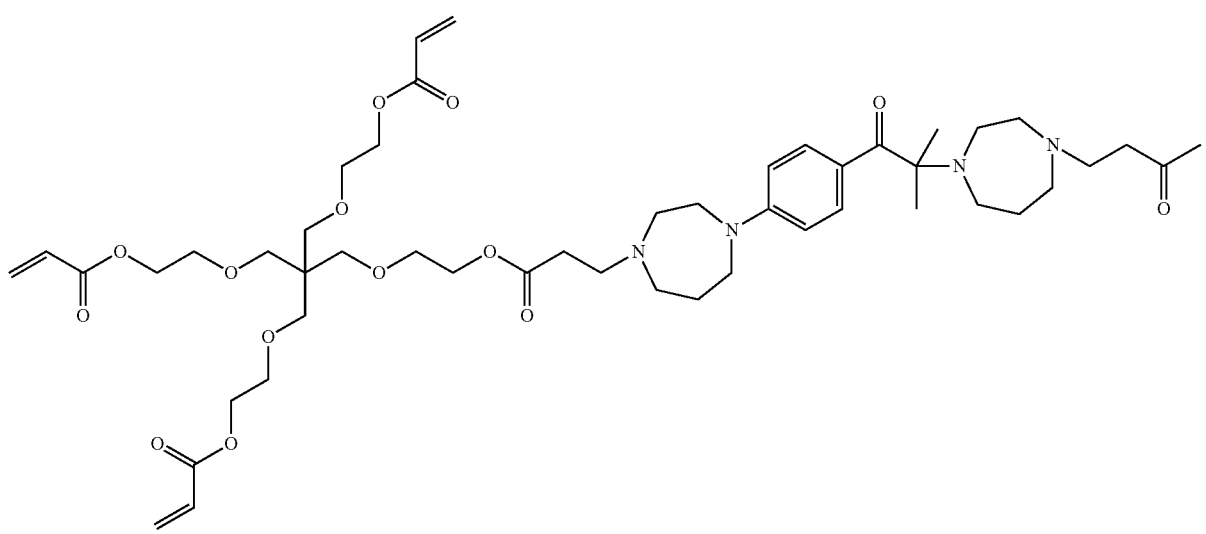

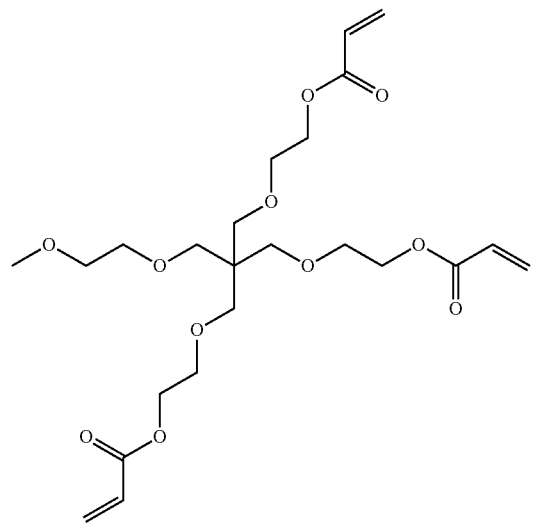

[Chem. 27]

(66)

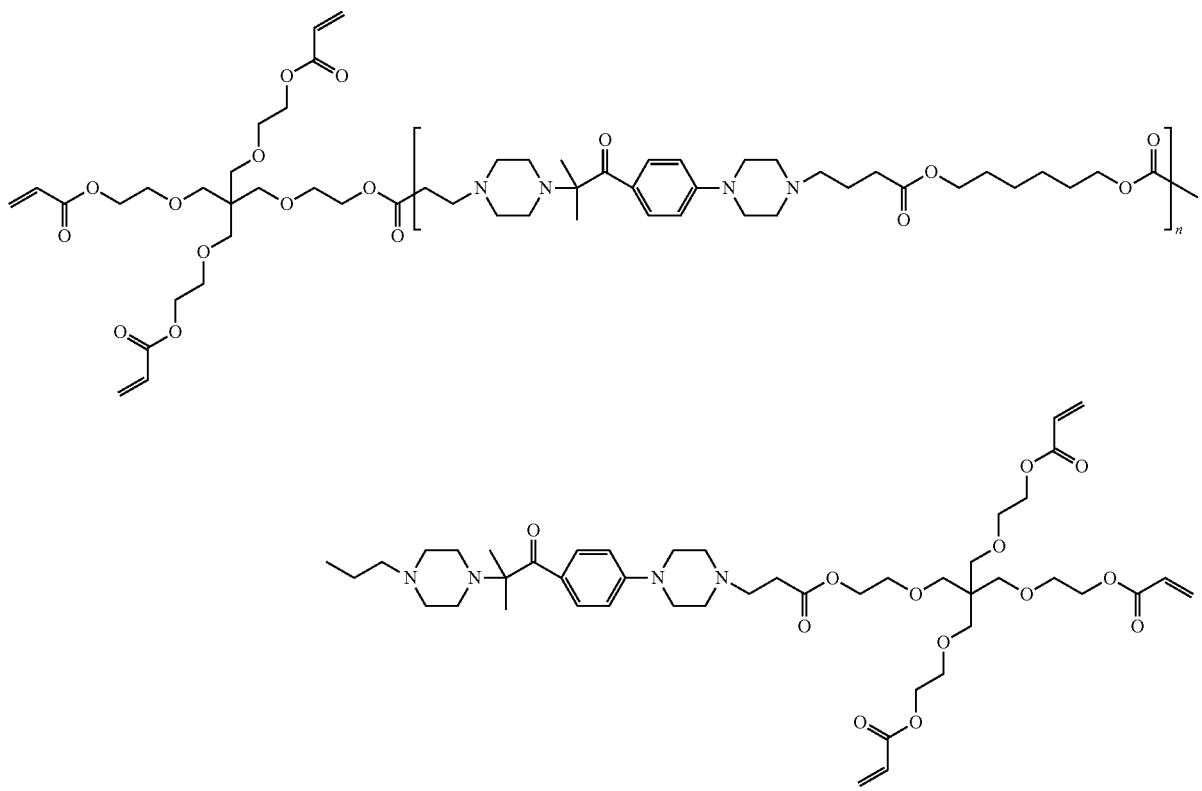

The Michael addition reaction product can be preferably used as a photoinitiator which suppresses migration and has excellent curability.

Next, an active energy ray-curable composition of the present invention is described.

An active energy ray-curable composition of the present invention is characterized by containing the Michael addition reaction product of the present invention and a radically curable monomer.

Examples of the radically curable monomer include ethylenic double bond-containing maleimide derivatives, maleate derivatives, fumarate derivatives, and (meth)acrylate derivatives. From the viewpoint of material availability and the curing rate, the (meth)acrylate derivatives are preferred.

The (meth)acrylate derivatives are not particularly limited, and the above-described various (meth)acrylate derivatives can be used.

The amount of the (meth)acrylate derivative used is 5 to 95 parts by mass relative to 5 to 95 parts by mass of the Michael addition reaction product. When the content of the Michael addition reaction product is less than 5 parts by mass, the curing performance tends to be impaired, while when the content of the (meth)acrylate derivative is less than 5 parts by mass, the physical properties of a coating film tend to deteriorate. Therefore, the content of the Michael addition reaction product of the present invention is preferably 10 to 90 parts by mass.

The active energy ray-curable composition of the present invention can be cured without addition of a general-purpose photoinitiator, but a photosensitizer may be used for further enhancing the curing performance. Examples of the photosensitizer include, but are not particularly limited to, thioxanthone compounds such as 2,4-diethylthioxanthone, 2,4-diisopropylthioxanthone, and the like; benzophenone compounds such as 4,4'-bis(diethylamino)benzophenone and the like; and anthraquinone.

If required, other components may be further added within a range not deviating from the object of the present invention, particularly within a range where storage stability, heat resistance, solvent resistance, etc. can be maintained. Examples of the other components which can be added include various coupling agents, an antioxidant, a stabilizer, a filler, and the like.

The coupling agents are compounds which enhance the function of a composite material by improving affinity through chemical bonding between an inorganic material and an organic material or chemical reaction. Examples of the coupling agents include silane compounds such as γ-(2-aminoethyl)aminopropyl trimethoxysilane, γ-(2-aminoethyl) aminopropylmethyl dimethoxysilane, γ-methacryloxypropyl trimethoxysilane, γ-glycidoxypropyl trimethoxysilane, and the like; titanium compounds such as tetra-isopropoxytitanium, tetra-n-butoxytitanium, and the like; and aluminum compounds such as aluminum isopropylate and the like. The amount of the coupling agent added is 0.1 to 10 parts by weight, preferably 0.2 to 5 parts by weight, relative to 100 parts by mass of the active energy ray-curable composition of the present invention.

Examples of the antioxidant include, but are not limited to, phenol antioxidants such as 2,6-di-tert-butyl-p-cresol, butylated hydroxyanisole, 2,4,6-tri-tert-butylphenol, 2,2'-methylene-bis(4-methyl-6-tert-butylphenol), and the like. The amount of the antioxidant added is 0.1 to 10 parts by weight, preferably 0.3 to 5 parts by weight, relative to 100 parts by mass of the active energy ray-curable composition of the present invention.

An appropriate solvent can be used for the active energy ray-curable composition of the present invention. The solvent is not particularly limited as long as it does not react with the components, and a single solvent or combination of two or more solvents may be used.

In order to produce the active energy ray-curable resin composition of the present invention, the above-described components may be mixed, and the mixing order and method are not particularly limited.

The active energy ray-curable composition of the present invention can be preferably used as a surface coating composition which coats a substrate surface. In this case, if required, various additives such as a mobility regulator such as silicon, polyamide, or the like, inorganic fine particles of silica, titanium oxide, zinc oxide, or the like, a silicon-, fluorine-, or acryl-based leveling agent, an ultraviolet absorber, an anti-dripping agent, a thickener, etc. can be mixed in usually used amounts.

Also, an excellent active energy ray-curable ink composition capable of significantly decreasing an odor and migration from an ink cured film can be produced by mixing a pigment and a printing ink resin with the active energy ray-curable composition of the present invention.

The pigment is not particularly limited, but an inorganic pigment and an organic pigment can be used. Examples of the inorganic pigment include chrome yellow, iron blue, barium sulfate, cadmium red, titanium oxide, zinc oxide, aluminum white, calcium carbonate, ultramarine blue, carbon black, graphite, colcothar, and the like. Examples of the organic pigment which can be used include various known common-use pigments such as β-naphthol pigments, β-oxynaphthoic acid pigments, azo pigments, phthalocyanine pigments, quinacridone pigments, dioxazine pigments, anthraquinone pigments, perylene pigments, metal complex pigments, and the like.

The printing ink resin is not particularly limited as long as it is dissolved in the active energy ray-curable ink composition of the present invention. For example, lipophilic polyester resins, petroleum resins, rosin ester resins, and the like can be used.

The active energy ray-curable ink composition of the present invention can be used for offset printing, gravure printing, flexographic printing, silk screen printing, and the like, but is particularly effective for offset printing. In use for an offset ink, a composition containing 10 to 80 parts by mass of a pigment and 20 to 100 parts by mass of vanish relative to 100 parts by mass of the active energy ray-curable composition can be used. However, in view of balance between a color density and printability of a printed matter, 20 to 70 parts by mass of a pigment and 30 to 80 parts by mass of vanish are preferably used relative to 100 parts by mass of the active energy ray-curable composition.

In addition, if required, various additives can be used. Typical examples of the additives include paraffin wax, polyethylene wax, polypropylene wax, polytetrafluoroethylene wax, silicon compounds, and the like, which are used for imparting an anti-friction property, an anti-blocking property, slippage, or scuff proof. Besides these, additives such as an ultraviolet absorber, an infrared absorber, an antibacterial agent, and the like can be added according to required performance.

The amount of each of the additives added is 0 to 10 parts by mass relative to 100 parts by mass of the active energy ray-curable ink composition of the present invention.

The active energy ray-curable ink composition of the present invention can be produced by mixing the components at normal temperature to 100° C. using a kneading/mixing/preparing machine such as a kneader, three rolls, a sand mill, or a gate mixer.

The active energy ray-curable composition, the active energy ray-curable surface coating composition, and the active energy ray-curable ink composition of the present invention can be polymerized and cured with active energy rays. The term "active energy rays" used refers to ultraviolet rays, ionizing radiation such as electron rays, α-rays, β-rays, and γ-rays, microwaves, high-frequency waves, visible light, infrared light, laser beams, and the like. Among these rays, ultraviolet rays are the active energy rays useful for polymerizing and curing the active energy ray-curable composition, the active energy ray-curable surface coating composition, and the active energy ray-curable ink composition of the present invention.

The ultraviolet rays at a wavelength of 180 to 400 nm are effective, but light at a wavelength of 254 nm, 308 nm, 313 nm, or 365 nm is particularly effective for curing the active energy ray-curable composition, the active energy ray-curable ink composition, and the active energy ray-curable surface coating composition of the present invention.

Examples of a light source include a low-pressure mercury lamp, a high-pressure mercury lamp, an extra-high-pressure mercury lamp, a metal halide lamp, a chemical lamp, a black light lamp, a mercury-xenon lamp, an excimer lamp, a short arc lamp, a helium-cadmium laser, an argon laser, an excimer laser, a LED lamp, and the like.

The quantity of ultraviolet irradiation is affected by the type of the light source used and the amount of the Michael addition reaction product of the present invention and thus cannot be unconditionally determined. However, from the viewpoint of productivity, the quantity is preferably in the range of 10 to 2000 $J/m^2$.

The active energy ray-curable composition, the active energy ray-curable surface coating composition, and the active energy ray-curable ink composition of the present invention are not required to use a general-purpose photoinitiator, and are thus very effective in view of safety and health because of no occurrence of a coating film odor, an extract from a cured coating film, and ink migration, which have been problems.

EXAMPLES

The present invention is described in further detail below with reference to examples, but the present invention is not limited to these examples.

Synthesis Example 1

Synthesis of 2-methyl-2-piperazinyl-1-(4-piperazinylphenyl)propan-1-one (9)

[Chem. 28]

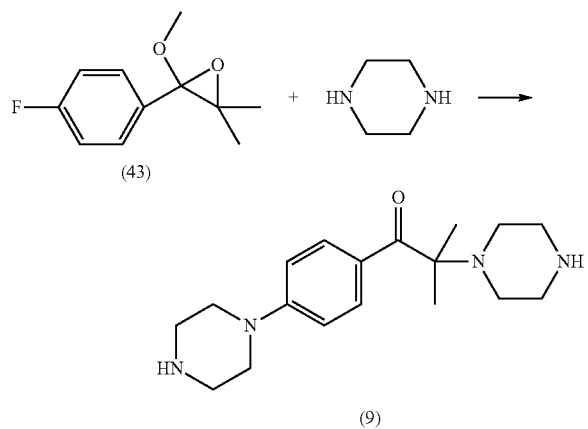

By a method described in Japanese Unexamined Patent Application Publication No. 60-84248, 2-(4-fluorophenyl)-3,3-dimethyl-2-methoxy-oxirane (43) was synthesized.

Next, in a 300 mL four-neck flask provided with a stirrer, a condenser, a thermocouple, a nitrogen inlet tube, and a dropping tube, 68 g of piperazine was added and heated to 160° C. under a nitrogen stream. Then, 23 g of (43) was added dropwise to piperazine at a rate of 4 mL/h over 5 hours and 15 minutes, followed by further stirring at the same temperature for 24 hours. After cooling, the reaction mixture was dissolved in 400 mL of dichloromethane and washed with 100 mL of water to separate an organic layer. An aqueous layer was washed with 100 mL of dichloromethane two times, and the whole organic layer was concentrated to produce 36 g of 2-methyl-2-piperazinyl-1-(4-piperazinylphenyl)propan-1-one (9).

$^1$H-NMR (CDCl$_3$): 1.25 ppm (s, 6H, —CH$_3$), 2.59 ppm (m, 4H, —CH$_2$—), 2.92 ppm (m, 4H, —CH$_2$—), 3.28 ppm (m, 4H, —CH$_2$), 3.91 ppm (s, 2H, NH), 3.98 ppm (m, 4H, —CH$_2$—), 6.86 ppm (m, 2H, aromatic), 8.58 ppm (m, 2H, aromatic)

Synthesis Example 2

Synthesis of 2-methyl-2-morpholin-4-yl-1-(4-piperazinylphenyl)propan-1-one (10)

[Chem. 29]

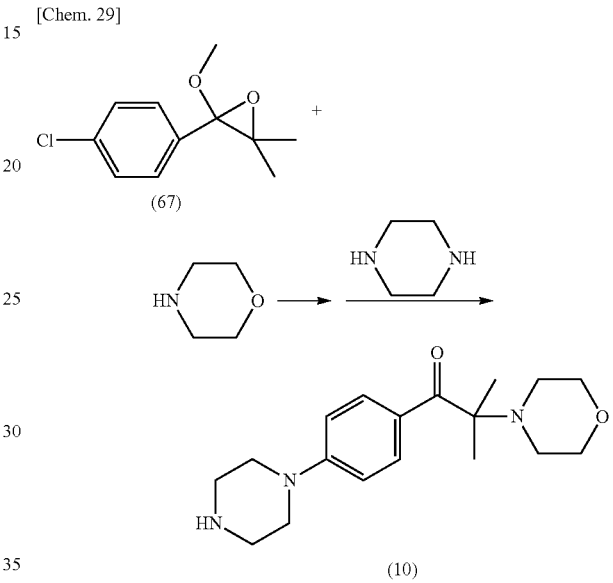

By a method described in Japanese Unexamined Patent Application Publication No. 60-84248, 2-(4-chlorophenyl)-3,3-dimethyl-2-methoxy-oxirane (67) was synthesized.

Next, in a 500 mL four-neck flask provided with a stirrer, a condenser, a thermocouple, and a nitrogen inlet tube, 80 g of compound (67) and 150 g of morpholine were added and stirred at 130° C. for 22 hours under a nitrogen stream. Then, excessive morpholine was distilled off at 130 to 160° C. under reduced pressure. The reaction product was dissolved in 200 mL of diethyl ether and washed with 200 mL of a 5% aqueous hydrochloric acid solution, and then an organic layer was dried with anhydrous sodium sulfate. The organic layer was concentrated and then purified by distillation to produce 80.5 g of 1-(4-chlorophenyl)-2-methyl-2-morpholino-propan-1-one.

Further, in a 300 mL four-neck flask provided with a stirrer, a condenser, a thermocouple, and a nitrogen inlet tube, 16 g of 1-(4-chlorophenyl)-2-methyl-2-morpholino-propan-1-one, 20.7 g of piperazine, 140 mg of palladium acetate, 360 mg of (2-biphenyl)di-tert-butylphosphine, 100 mL of toluene, 40 mL of THF, and 9.4 mg of potassium-tert-butoxide were added, followed by reaction at room temperature for 46 hours under a nitrogen stream. The reaction product was diluted with 100 mL of diethyl ether and washed with 100 mL of water, and then an organic layer was dried with anhydrous sodium sulfate. The organic layer was concentrated and then recrystallized with dichloromethane/hexane to produce 18.3 g of 2-methyl-2-morpholin-4-yl-1-(4-piperazinylphenyl) propan-1-one (10). $^1$H-NMR (CDCl$_3$): 1.34 ppm (s, 6H, —CH$_3$), 2.60 ppm (m, 4H, —CH$_2$—), 3.05 ppm (m, 4H, —

CH$_2$—), 3.34 ppm (m, 4H, —CH$_2$—), 3.72 ppm (m, 4H, —CH$_2$), 6.86 ppm (m, 2H, aromatic), 8.58 ppm (m, 2H, aromatic)

Synthesis Example 3

Synthesis of 1-(4-mercaptophenyl)-2-methyl-2-morpholino-propan-1-one (11)

[Chem. 30]

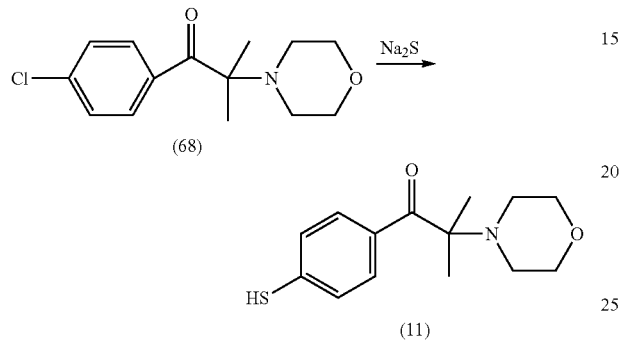

In a 500 mL four-neck flask provided with a stirrer, a condenser, a thermocouple, and a nitrogen inlet tube, 240 g of N-methylpyrrolidone and 88 g of sodium sulfide were added and heated to 75° C. Then, 40 g of 1-(4-chlorophenyl)-2-methyl-2-morpholino-propan-1-one (68) produced in Synthesis Example 2 was added dropwise, followed by reaction at 130° C. for 2 hours. After the reaction product was cooled to room temperature, the reaction product was added to 400 mL of ice water and neutralized to pH 6 to 7 with a 15% hydrochloric acid solution while being vigorously stirred by nitrogen blowing. After further stirring for 1 hour, the mixture was extracted with 250 mL of diethyl ether two times, and an organic layer was concentrated to about 200 mL.

Next, the organic layer was extracted three times with 60 mL of a 20% aqueous sodium hydroxide solution. The resultant aqueous layer was neutralized with a 20% hydrochloric acid solution under cooling. Then, the aqueous layer was extracted three times with 100 mL of diethyl ether, and the resultant organic layer was dried with anhydrous sodium sulfate and concentrated to produce 19.8 g of 1-(4-mercaptophenyl)-2-methyl-2-morpholino-propan-1-one (11). $^1$H-NMR (CDCl$_3$): 1.4 ppm (s, 6H, —CH$_3$), 2.6 ppm (m, 4H, —CH$_2$—), 3.8 ppm (m, 4H, —CH$_2$—), 7.5 ppm (d, 2H, aromatic), 8.6 ppm (m, 2H, aromatic)

Synthesis Example 4

Synthesis of 2-methyl-1-(4-methylsulfanylphenyl)-2-piperazin-1-yl-propan-1-one (12)

[Chem. 31]

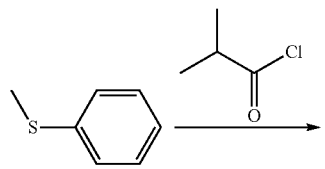

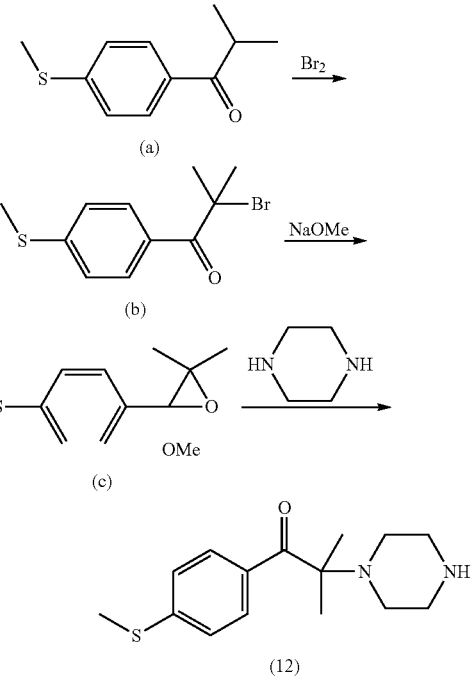

In a 500 mL four-neck flask provided with a stirrer, a condenser, a thermocouple, and a dropping funnel, 34.6 g of aluminum trichloride and 100 mL of o-dichlorobenzene were added and cooled to 8° C. Then, 29.5 g of isobutyric acid chloride was added dropwise over 30 minutes. After stirring at about 10° C. for 30 minutes, 32.3 g of thioanisole was added dropwise at the same temperature over 2 hours. Then, 160 mL of a 5% hydrochloric acid solution was added dropwise so that the temperature did not exceed 20° C., followed by stirring overnight at room temperature. An organic layer was separated, and then an aqueous layer was extracted with 20 mL of o-chlorobenzene. The whole organic layer was dried with anhydrous sodium sulfate, concentrated, and then distilled to produce 50.1 g of 2-methyl-1-(4-methylsulfanylphenyl)-1-propan-1-one (a).

Next, in a 500 mL four-neck flask provided with a stirrer, a condenser, and a thermocouple, 49.2 g of the compound (a) and 60 mL of chloroform were added, and 41.5 g of bromine was added dropwise at room temperature over 2 hours, followed by further stirring for 2 hours. The reaction solution was washed with 10% sodium hydrogen carbonate, and the resultant organic layer was dried with anhydrous sodium sulfate and concentrated to produce 63.5 g of 2-bromo-2-methyl-1-(4-methylsulfanylphenyl)-1-propan-1-one (b).

Next, in a 300 mL four-neck flask provided with a stirrer, a condenser, a thermocouple, and a dropping funnel, 41.5 g of sodium methoxide and 60 mL of methanol were added, and the resultant mixture was stirred at 40° C. Then, 61.7 g of the compound (b) was added over 4 hours, followed by further stirring for 1 hour. Then, 100 mL of ice water was added to the mixture, and the precipitated crystals were filtered off and dried under reduced pressure to produce 50.9 g of 2-methoxy-3,3-dimethyl-2-(4-methylsulfanylphenyl)-oxirane (c).

Further, in a 500 mL four-neck flask provided with a stirrer, a condenser, and a thermocouple, the compound (c) and 31 g of piperazine were added, followed by stirring at 130° C. for 6 hours. After cooling, 80 mL of dichloromethane was added, and an organic layer was washed three times with 70 mL of water. The organic layer was dried with anhydrous sodium sulfate and concentrated to produce 60.7 g of 2-methyl-1-(4-methylsulfanylphenyl)-2-piperazin-1-yl-propan-1-one (12).

$^1$H-NMR (CDCl$_3$): 1.4 ppm (s, 6H, —CH$_3$), 2.6 ppm (s, 3H, —CH$_3$), 2.7 ppm (t, 4H, —CH$_2$—), 3.1 ppm (t, 4H, —CH$_2$—), 7.3 ppm (d, 2H, aromatic), 8.5 ppm (m, 2H, aromatic)

Synthesis Example 5

Synthesis of 2-dimethylamino-2-(4-piperazin-1-yl-benzyl)-1-(4-piperazin-1-yl-phenyl)-butan-1-one (13)

[Chem. 32]

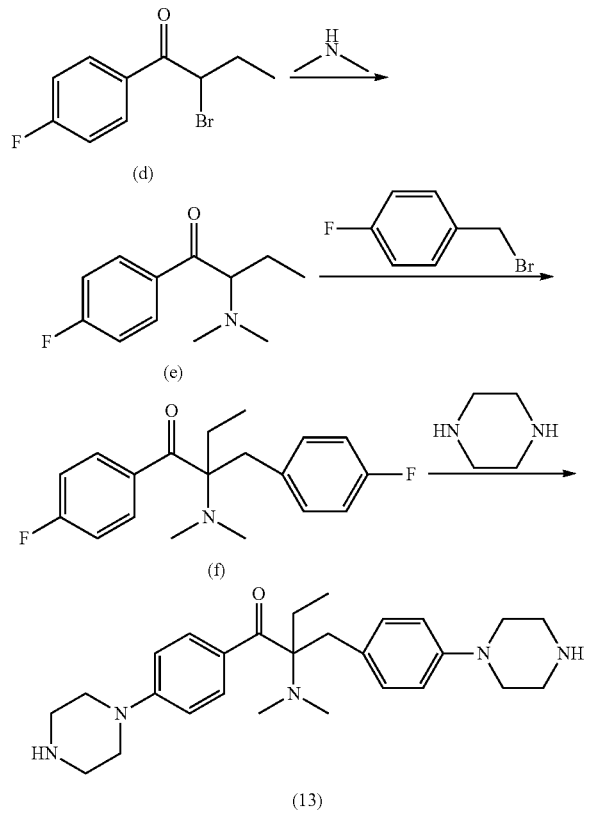

In a 1 L four-neck flask provided with a stirrer, a condenser, and a thermocouple, 400 mL of methylethyl ketone, 104 g of potassium carbonate, and 122 g of 1-(4-fluorophenyl)-2-bromobutan-1-one (d) synthesized by a method described in European Patent No. 3002 were added and stirred at 50° C. Then, 29 g of dimethylamine was blown into the resultant suspension over 2 hours. After further reaction at the same temperature for 5 hours, the reaction solution was poured into 400 mL of water and stirred for 30 minutes. After stirring was stopped, an organic layer was dried with anhydrous sodium sulfate and concentrated to produce 95 g of 2-dimethylamino-1-(4-fluorophenyl)-1-butan-1-one (e).

Next, in a 1 L four-neck flask provided with a stirrer, a condenser, a thermocouple, and a dropping funnel, 300 mL of methyl ethyl ketone and 84 g of the compound (e) were stirred at 50° C., and 79 g of 4-fluorobenzyl bromide was added dropwise to the resultant mixture over 20 minutes. After further stirring at the same temperature for 4 hours, the resultant mixture was heated to 60° C., and 32 g of sodium hydroxide was added over 45 minutes. The reaction solution was stirred at 50° C. for 2 hours and then added to 100 mL of water, followed by stirring for 30 minutes. After stirring was stopped, an organic layer was dried with anhydrous sodium sulfate and concentrated to produce a crude reaction product. The reaction product was recrystallized with ethanol and then filtered off to produce 98 g of 2-(4-fluorobenzyl)-2-dimethylamino-1-(4-fluorophenyl)-1-butan-1-one (f).

Next, in a 500 mL four-neck flask provided with a stirrer, a condenser, and a thermocouple, 95 g of the compound (f) and 206 g of piperazine were added, and the resultant mixture was stirred at 130° C. for 6 hours. After cooling, 150 mL of dichloromethane was added, and an organic layer was washed three times with 150 mL of water. The organic layer was dried with anhydrous sodium sulfate, concentrated, and recrystallized with ethyl acetate/hexane to produce 68 g of 2-dimethylamino-2-(4-piperazin-1-yl-benzyl)-1-(4-piperazin-1-yl-phenyl)-butan-1-one (13). $^1$H-NMR (CDCl$_3$): 0.9 ppm (t, 3H, —CH$_3$), 1.5 ppm (q, 2H, —CH$_2$), 2.3 ppm (s, 6H, N—CH$_3$), 2.6-2.9 ppm (m, 10H, Ph-CH$_2$, N—CH$_2$), 3.5 ppm (m, 8H, N—CH$_2$—), 6.7-6.8 ppm (m, 4H, aromatic), 7.1 ppm (d, 2H, aromatic), 7.8 ppm (d, 2H, aromatic)

Synthesis Example 6

Synthesis of 2-phenyl-2-piperazin-1-yl-1-(4-piperazin-1-yl-phenyl)-butan-1-one (14)

[Chem. 33]

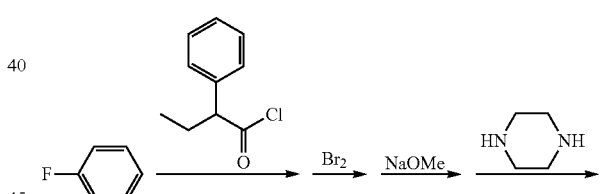

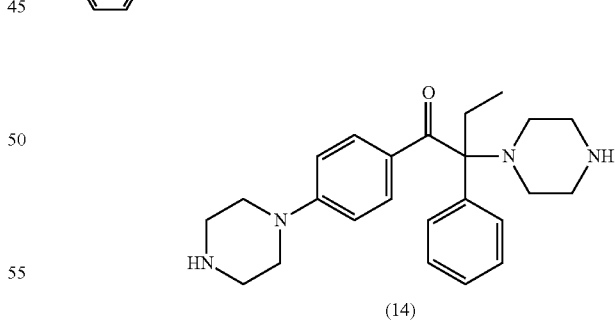

According to the method described in Synthesis Example 4 except that 51.4 g of 2-phenylbutyric acid chloride and 25 g of fluorobenzene were used in place of 29.5 g of isobutyric acid chloride and 32.3 g of thioanisole, respectively, used in Synthesis Example 4, 78.5 g of 2-phenyl-2-piperazin-1-yl-1-(4-piperazin-1-yl-phenyl)-butan-1-one (14) was produced.

$^1$H-NMR (CDCl$_3$): 0.9 ppm (t, 3H, —CH$_3$), 1.9 ppm (q, 2H, —CH$_2$), 2.6-2.8 ppm (m, 12H, N—CH$_2$), 3.5 ppm (t, 4H, N—CH$_2$), 6.8 ppm (d, 2H, aromatic), 7.3-7.4 ppm (m, 5H, aromatic), 8.5 ppm (d, 2H, aromatic)

Synthesis Example 7

Synthesis of 2-methyl-2-piperazin-1-yl-1-(4-piperazin-1-yl-phenyl)-butan-1-one (15)

[Chem. 34]

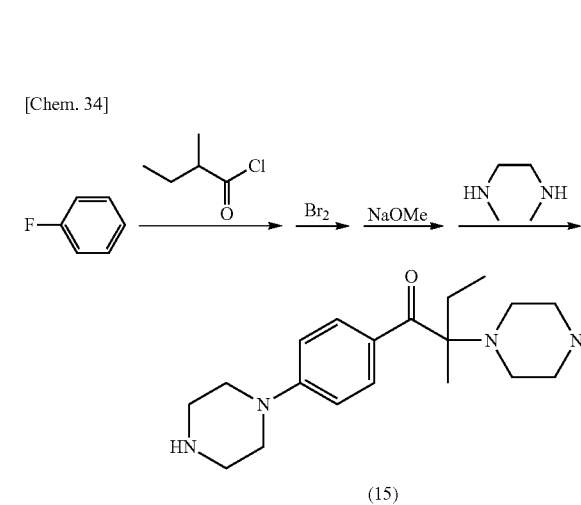

(15)

According to the method described in Synthesis Example 6 except that 33.7 g of 2-methylbutyric acid chloride was used in place of 51.4 g of 2-phenylbutyric acid chloride used in Synthesis Example 6, 48.3 g of 2-methyl-2-piperazin-1-yl-1-(4-piperazin-1-yl-phenyl)-butan-1-one (15) was produced.

$^1$H-NMR (CDCl$_3$): 0.9 ppm (t, 3H, —CH$_3$), 1.3 ppm (s, 3H, —CH$_3$), 1.5 ppm (q, 2H, —CH$_2$), 2.6-2.8 ppm (m, 12H, N—CH$_2$), 3.5 ppm (t, 4H, N—CH$_2$—), 6.8 ppm (d, 2H, aromatic), 8.5 ppm (d, 2H, aromatic)

Synthesis Example 8

Synthesis of (1-piperazin-1-yl-1-cyclohexyl)-(4-piperazin-1-yl-phenyl)-methanone (16)

[Chem. 35]

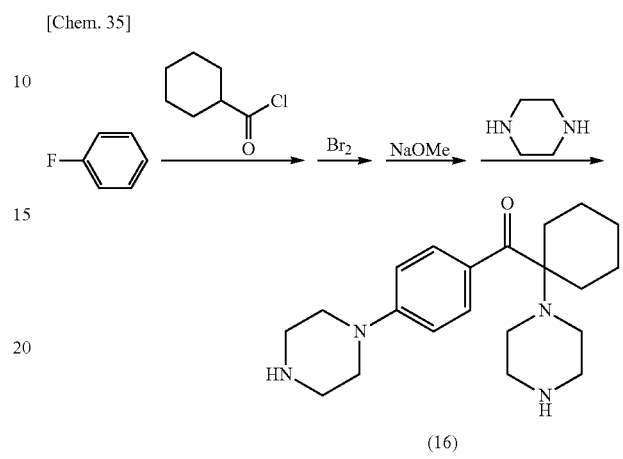

(16)

According to the method described in Synthesis Example 6 except that 37.4 g of cyclohexylcarboxylic acid chloride was used in place of 51.4 g of 2-phenylbutyric acid chloride used in Synthesis Example 6, 43.1 g of (1-piperazin-1-yl-1-cyclohexyl)-(4-piperazin-1-yl-phenyl)-methanone (16) was produced.

$^1$H-NMR (CDCl$_2$): 1.4-1.7 ppm (m, 10H, —CH$_2$), 2.4 ppm (t, 4H, N—CH$_2$—), 2.6-2.8 ppm (m, 8H, N—CH$_2$), 3.5 ppm (t, 4H, N—CH$_2$—), 6.8 ppm (d, 2H, aromatic), 8.5 ppm (d, 2H, aromatic)

Synthesis Example 9

Synthesis of 2-methyl-2-piperazin-1-yl-1-(4-piperazin-1-yl-phenyl)-pent-4-en-1-one (17)

[Chem. 36]

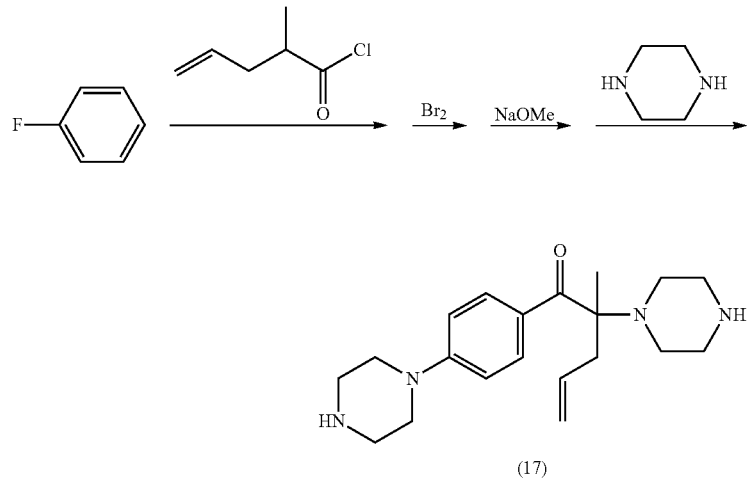

(17)

According to the method described in Synthesis Example 6 except that 37.1 g of 2-methyl-4-pentenoyl chloride was used in place of 51.4 g of 2-phenylbutyric acid chloride used in Synthesis Example 6, 43.1 g of 2-methyl-2-piperazin-1-yl-1-(4-piperazin-1-yl-phenyl)-pent-4-en-1-one (17) was produced.

$^1$H-NMR (CDCl$_3$): 1.3 ppm (s, 3H, —CH$_3$), 2.0-2.1 ppm (m, 2H, —CH$_2$), 2.6-2.8 ppm (m, 12H, N—$\overline{CH_2}$), 3.5 ppm (t, 4H, N—$\overline{CH_2}$—), 5.0 ppm (t, 2H, =CH$_2$), 5.8 ppm (m, 1H, =$\overline{CH_2}$—), $\overline{6.8}$ ppm (d, 2H, aromatic), $\overline{8.5}$ ppm (d, 2H, aromatic)

Synthesis Example 10

Synthesis of 2-methyl-2-[methyl-(2-methylamino-ethyl)-amino]-1-{4-[methyl-(2-methylamino-ethyl)-amino]-phenyl}-propan-1-one (18)

[Chem. 37]

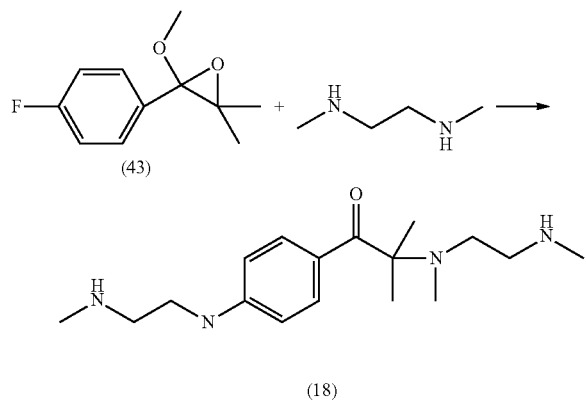

According to the method described in Synthesis Example 1 except that 69 g of dimethylaminoethane was used in place of 68 g of piperazine used in Synthesis Example 1, 32 g of 2-methyl-2-[methyl-(2-methylamino-ethyl)-amino]-1-{4-[methyl-(2-methylamino-ethyl)-amino]-phenyl}-propan-1-one (18) was produced.

$^1$H-NMR (CDCl$_3$): 1.3 ppm (s, 6H, —CH$_3$), 2.3 ppm (s, 3H, —N—CH$_3$), 2.4-2.6 ppm (m, 6H, —N$\overline{=CH_2}$), 2.8 ppm (s, 3H, —N$\overline{=CH_3}$), 3.5 ppm (t, 4H, N—CH$_2$—), 6.8 ppm (d, 2H, aromatic), $\overline{8.5}$ ppm (d, 2H, aromatic)

Synthesis Example 11

Synthesis of 2-methyl-2-perhydro-1,4-diazepin-1-yl-1-(4-perhydro-1,4-diazepin-1-yl-phenyl)-propan-1-one (19)

[Chem. 38]

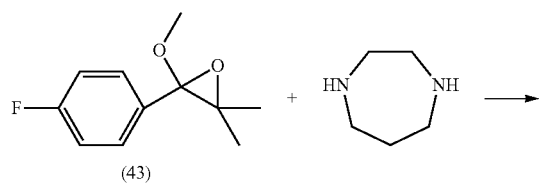

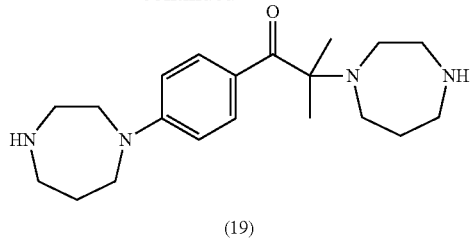

According to the method described in Synthesis Example 1 except that 80 g of perhydro-1,4-diazepine was used in place of 68 g of piperazine used in Synthesis Example 1, 42 g of 2-methyl-2-perhydro-1,4-diazepin-1-yl-1-(4-perhydro-1,4-diazepin-1-yl-phenyl)-propan-1-one (19) was produced.

$^1$H-NMR (CDCl$_3$): 1.3 ppm (s, 6H, —CH$_3$), 1.5-1.6 ppm (m, 4H, —CH$_2$), 2.5-2.7 ppm (m, 8H, —N$\overline{=CH_2}$), 2.8 ppm (t, 2H, N$\overline{=CH_2}$—), 3.1 ppm (t, 2H, N—CH$_2$), $\overline{3.5}$ ppm (t, 2H, N—CH$_2$—), 3.9 ppm (t, 2H, N—CH$_2$—), 6.8 ppm (d, 2H, aromatic), 8.5 ppm (d, 2H, aromatic)

Example 1

In a 100 mL three-neck flask provided with a stirrer, a condenser, and a thermocouple, 32 g of ethylene oxide-modified pentaerythritol tetraacrylate (Miramer 4004 manufactured by MIWON Co., Ltd.) and 8 g of the phenyl ketone derivative (9) produced in Synthesis Example (1) were added and stirred at room temperature for 24 hours to produce 40 g of a Michael addition reaction product of the present invention (the compound (45) described above). During reaction preparation, a ratio between groups functioning as a Michael donor and groups functioning as a Michael acceptor was 1:4.8.

Example 2

In a 100 mL three-neck flask provided with a stirrer, a condenser, and a thermocouple, 32 g of ditrimethylolpropane tetraacrylate (KAYARAD T1420 manufactured by Nippon Kayaku Co., Ltd.) and 8 g of the phenyl ketone derivative (10) produced in Synthesis Example (2) were added and stirred at room temperature for 24 hours to produce 40 g of a Michael addition reaction product of the present invention (the compound (46) described above). During reaction preparation, a ratio between groups functioning as a Michael donor and groups functioning as a Michael acceptor was 1:10.9.

Example 3

In a 100 mL three-neck flask provided with a stirrer, a condenser, and a thermocouple, 28 g of ethylene oxide-modified trimethylolpropane (ARONIX M-350 manufactured by Toagosei Co., Ltd.) and 12 g of the phenyl ketone derivative (11) produced in Synthesis Example (3) were added and stirred at 80° C., and then 1 g of 1,8-diazabicyclo[5.4.0]undecene was gradually added to the resultant mixture. The mixture was stirred at the same temperature for 6 hours to produce 40 g of a Michael addition reaction product of the present invention (the compound (47) described above). During reaction preparation, a ratio between groups functioning as a Michael donor and groups functioning as a Michael acceptor was 1:4.3.

Example 4

In a 100 mL three-neck flask provided with a stirrer, a condenser, and a thermocouple, 32 g of dipentaerythritol hexaacrylate (ARONIX M-405 manufactured by Toagosei Co., Ltd.) and 8 g of the phenyl ketone derivative (12) produced in Synthesis Example (4) were added and stirred at room temperature for 24 hours to produce 40 g of a Michael addition reaction product of the present invention (the compound (48) described above). During reaction preparation, a ratio between groups functioning as a Michael donor and groups functioning as a Michael acceptor was 1:11.5.

Example 5

In a 100 mL three-neck flask provided with a stirrer, a condenser, and a thermocouple, 34 g of ethylene oxide-modified pentaerythritol tetraacrylate (Miramar 4004 manufactured by MIWON Co., Ltd.) and 6 g of the phenyl ketone derivative (13) produced in Synthesis Example (5) were added and stirred at room temperature for 24 hours to produce 40 g of a Michael addition reaction product of the present invention (the compound (59) described above). During reaction preparation, a ratio between groups functioning as a Michael donor and groups functioning as a Michael acceptor was 1:8.7.

Example 6

In a 100 mL three-neck flask provided with a stirrer, a condenser, and a thermocouple, 32 g of ditrimethylolpropane tetraacrylate (KAYARAD T1420 manufactured by Nippon Kayaku Co., Ltd.) and 8 g of the phenyl ketone derivative (14) produced in Synthesis Example (6) were added and stirred at room temperature for 24 hours to produce 40 g of a Michael addition reaction product of the present invention (the compound (60) described above). During reaction preparation, a ratio between groups functioning as a Michael donor and groups functioning as a Michael acceptor was 1:6.7.

Example 7

In a 100 mL three-neck flask provided with a stirrer, a condenser, and a thermocouple, 35 g of dipentaerythritol hexaacrylate (ARONIX M-405 manufactured by Toagosei Co., Ltd.) and 5 g of the phenyl ketone derivative (15) produced in Synthesis Example (7) were added and stirred at room temperature for 24 hours to produce 40 g of a Michael addition reaction product of the present invention (the compound (61) described above). During reaction preparation, a ratio between groups functioning as a Michael donor and groups functioning as a Michael acceptor was 1:12.

Example 8

In a 100 mL three-neck flask provided with a stirrer, a condenser, and a thermocouple, 30 g of pentaerythritol triacrylate (ARONIX M-305 manufactured by Toagosei Co., Ltd.) and 10 g of the phenyl ketone derivative (16) produced in Synthesis Example (8) were added and stirred at room temperature for 24 hours to produce 40 g of a Michael addition reaction product of the present invention (the compound (62) described above). During reaction preparation, a ratio between groups functioning as a Michael donor and groups functioning as a Michael acceptor was 1:5.4.

Example 9

In a 100 mL three-neck flask provided with a stirrer, a condenser, and a thermocouple, 34 g of trimethylolpropane triacrylate (ARONIX M-309 manufactured by Toagosei Co., Ltd.) and 6 g of the phenyl ketone derivative (17) produced in Synthesis Example (9) were added and stirred at room temperature for 24 hours to produce 40 g of a Michael addition reaction product of the present invention (the compound (63) described above). During reaction preparation, a ratio between groups functioning as a Michael donor and groups functioning as a Michael acceptor was 1:10.2.

Example 10

In a 100 mL three-neck flask provided with a stirrer, a condenser, and a thermocouple, 31 g of ethylene oxide-modified trimethylolpropane triacrylate (ARONIX M-350 manufactured by Toagosei Co., Ltd.) and 9 g of the phenyl ketone derivative (18) produced in Synthesis Example (10) were added and stirred at room temperature for 24 hours to produce 40 g of a Michael addition reaction product of the present invention (the compound (64) described above). During reaction preparation, a ratio between groups functioning as a Michael donor and groups functioning as a Michael acceptor was 1:3.9.

Example 11

In a 100 mL three-neck flask provided with a stirrer, a condenser, and a thermocouple, 33 g of ethylene oxide-modified pentaerythritol tetraacrylate (Miramar 4004 manufactured by MIWON Co., Ltd.) and 7 g of the phenyl ketone derivative (19) produced in Synthesis Example (11) were added and stirred at room temperature for 24 hours to produce 40 g of a Michael addition reaction product of the present invention (the compound (65) described above). During reaction preparation, a ratio between groups functioning as a Michael donor and groups functioning as a Michael acceptor was 1:6.1.

Example 12

In a 100 mL three-neck flask provided with a stirrer, a condenser, and a thermocouple, 9.0 g of hexanediol diacrylate (VISCOAT 230D manufactured by Osaka Organic Chemical Industry Ltd.) and 12.5 g of the phenyl ketone derivative (9) produced in Synthesis Example (1) were added and stirred at room temperature for 24 hours. Then, 14 g of ethylene oxide-modified pentaerythritol tetraacrylate (Miramar 4004 manufactured by MIWON Co., Ltd.) was added to the reaction mixture and further stirred at room temperature for 24 hours to produce 35.5 g of a Michael addition reaction product of the present invention (the compound (66) described above). During reaction preparation, a ratio between groups functioning as a Michael donor and groups functioning as a Michael acceptor was 1:2.

Comparative Synthesis Example 1

Synthesis of Compound (69) Described in Related Art and Michael Addition Reaction Product Thereof For comparative investigation, a compound described in related art (PTL 3: Japanese Unexamined Patent Application Publication (Translation of PCT Application) No. 2007-534800) and a Michael addition reaction product thereof were synthesized.

[Chem. 39]

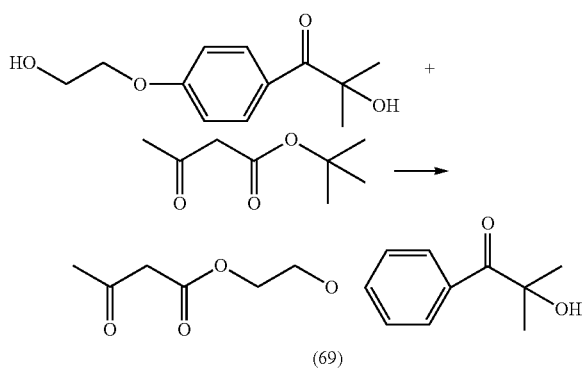

(69)

In a 2 L four-neck flask provided with a stirrer, a condenser, a thermocouple, and a nitrogen inlet tube, 250 mL of toluene and 224.25 g of IRGACURE 2959 of Ciba Specialty Chemicals Inc. were added and stirred at room temperature. Then, 158.2 g of tert-butyl acetoacetate was added to the resultant mixture, followed by stirring at 110° C. for 1 hour.

Next, a distillation tube was attached to a reactor, and a toluene/tert-butanol azeotropic mixture was distilled off under a nitrogen stream until the inner temperature was 125° C. When the inner temperature reached 125° C., reaction was terminated, and the solvent was distilled off from the resultant reaction mixture to produce 309 g of a photoinitiator (69) described in the related art.

Next, in a 200 mL three-neck flask provided with a stirrer, a condenser, and a thermocouple, 64 g of ethylene oxide-modified pentaerythritol tetraacrylate (Miramer 4004), 16 g of the compound (69), and 0.67 g of tetrabutylammonium bromide were added and stirred at room temperature for 24 hours to produce 80 g of Michael addition reaction product (A). During reaction preparation, a ratio between groups functioning as a Michael donor and groups functioning as a Michael acceptor was 1:9.3.

Examples 13 to 21

Evaluation as Surface Coating Composition

The Michael addition reaction products (45) to (48) and (59) to (66) produced in Examples 1 to 12 were mixed to have compositions shown in Table 1, preparing UV curable compositions. The compositions were cured with a conveyor-type ultraviolet irradiation device (manufactured by Eye Graphics Co., Ltd.) provided with a 120 W/cm high-pressure mercury lamp, leading to the evaluation results shown in Tables 1 and 2.

(Evaluation Method)

[Quantity of UV irradiation required for curing]: An amount of UV irradiation required for making a coating film of 5 μm in thickness tack-free was measured.

[Gel fraction of cured film]: A coating film of 50 μm in thickness was formed with an amount of UV irradiation of 200 mJ/cm$^2$, the resultant cured film was separated from a substrate, and a residual ratio was determined by measuring the weight of the cured coating film before and after extraction of the cured film in ethanol under reflux for 3 hours.

[MEK rubbing of cured film]: A coating film of 5 μm in thickness was formed with an amount of UV irradiation of 100 mJ/cm$^2$, and the number of rubbing cycles required until the coating film was broken by surface rubbing with a cotton swab soaked in MEK.

[Odor of cured film]: An odor of a coating film cured with an amount of UV irradiation of 100 mJ/cm$^2$ was evaluated in four levels.

1: No odor, 2: Slight odor, 3: Distinct odor, 4: Strong order

TABLE 1

|  | Example 13 | Example 14 | Example 15 | Example 16 |
|---|---|---|---|---|
| Michael addition reaction product 45 | 30 |  |  |  |
| Michael addition reaction product 46 |  | 30 |  |  |
| Michael addition reaction product 47 |  |  | 20 |  |
| Michael addition reaction product 48 |  |  |  | 30 |
| Miramer 4004 | 75 | 75 | 85 | 75 |
| Amount of UV irradiation required for curing (mJ/cm$^2$) | 50 | 60 | 60 | 50 |
| Gel fraction of cured film | 99.4% | 99.2% | 99.5% | 99.2% |
| MEK rubbing of cured film | >30 times | >30 times | >30 times | >30 times |
| Odor of cured film | 1 | 1 | 1 | 1 |

TABLE 2

|  | Example 17 | Example 18 | Example 19 | Example 20 | Example 21 |
|---|---|---|---|---|---|
| Michael addition reaction product 62 | 20 |  |  |  |  |
| Michael addition reaction product 63 |  | 30 |  |  |  |
| Michael addition reaction product 64 |  |  | 15 |  |  |
| Michael addition reaction product 65 |  |  |  | 20 |  |
| Michael addition reaction product 66 |  |  |  |  | 15 |
| Miramer 4004 | 85 | 75 | 90 | 85 | 85 |
| Amount of UV irradiation required for curing (mJ/cm$^2$) | 60 | 55 | 70 | 60 | 40 |
| Gel fraction of cured film | 99.3% | 99.5% | 99.2% | 99.2% | 99.3% |
| MEK rubbing of cured film | >30 times | >30 times | >30 times | >30 times | >30 times |
| Odor of cured film | 1 | 1 | 1 | 1 | 1 |

<Description of Compounds Shown in Tables>

Michael addition reaction product 45: Michael addition reaction product produced in Example 1
Michael addition reaction product 46: Michael addition reaction product produced in Example 2
Michael addition reaction product 47: Michael addition reaction product produced in Example 3
Michael addition reaction product 48: Michael addition reaction product produced in Example 4
Michael addition reaction product 62: Michael addition reaction product produced in Example 8
Michael addition reaction product 63: Michael addition reaction product produced in Example 9
Michael addition reaction product 64: Michael addition reaction product produced in Example 10
Michael addition reaction product 65: Michael addition reaction product produced in Example 11
Michael addition reaction product 66: Michael addition reaction product produced in Example 12
Miramer 4004: Ethylene oxide-modified pentaerythritol tetraacrylate manufactured by MIWON Co., Ltd.

Comparative Examples 1 to 3

The Michael addition reaction product (A) produced in Comparative Synthesis Example 1, general-purpose photoinitiator Irgacure 907 (2-methyl-1-[4-(methylthio)phenyl]-2-morpholinopropan-1-one: manufactured by Ciba Specialty Inc.), and Esacure KIP-150 (high-molecular-weight type photoinitiator manufactured by Lamberti Inc.) were mixed to have compositions shown in Table 3. The results of the same evaluation as in the examples are shown in Table 3.

TABLE 3

|  | Comparative Example 1 | Comparative Example 2 | Comparative Example 3 |
|---|---|---|---|
| Michael addition reaction product A | 30 | | |
| Miramer 4004 | 75 | 100 | 100 |
| Irgacure 907 | | 5 | |
| KIP-150 | | | 5 |
| Amount of UV irradiation required for curing (mJ/cm$^2$) | 220 | 40 | 40 |
| Gel fraction of cured film | 84% | 98% | 98.5% |
| MEK rubbing of cured film | >2 times | >30 times | >30 times |
| Odor of cured film | 1 | 4 | 2 |

<Description of Compounds Shown in Table>

Michael addition reaction product A: Michael addition reaction product produced in Comparative Synthesis Example 1
Miramer 4004: Ethylene oxide-modified pentaerythritol tetraacrylate manufactured by MIWON Co., Ltd.
Irgacure 907: 2-methyl-1-[4-(methylthio)phenyl]-2-morpholinopropan-1-one manufactured by Ciba Specialty Inc.
KIP-150: high-molecular-weight photoinitiator manufactured by Lamberti Inc.

The UV curable resin compositions of the present invention have practical curing performance and are excellent in a coating film order and an amount (gel fraction) of material eluted from a coating film. On the other hand, it is obvious that the compositions of the comparative examples have the problems of poor curing performance, large amounts of extracts from coating films, strong odors of coating films, etc.

Examples 22 to 26

Evaluation as UV Curable Ink

Materials shown in Tables 4 and 5 were mixed and kneaded with three rolls to produce UV curable inks. Tests described below were performed for the UV curable inks.

[Curability]: A UV ink (0.125 cc/using three cut roll) was drawn down on PET tack paper using a RI tester drawdown machine and ultraviolet irradiation was performed using a conveyor-type ultraviolet irradiation device provided with a 120 W/cm metal halide lamp. A surface of the ink film after curing was rubbed with paper, and a conveyor speed at which the ink was not transferred to the paper was evaluated as curability based on the following criteria:
Circle: Curability of 60 m/min or more
Triangle: Curability of 30 to 60 m/min
Cross: Curability of 30 m/min or less

[Solvent resistance]: Drawdown was performed under the same conditions as described above, and ultraviolet irradiation was performed at a speed of 40 m/min using a conveyor-type ultraviolet irradiation device provided with a 120 W/cm metal halide lamp to prepare an evaluation sample. A surface of the sample was rubbed with a cotton swab soaked in MEK, and the number of rubbing cycles when the ink film was peeled was evaluated as solvent resistance.

[Gloss]: Gloss at 60° and –60° was measured with a reflective glass meter (manufactured by Murakami Color Research Laboratory).

[Cured film odor]: The sample subjected to the evaluation of solvent resistance was smelled to evaluate the odor on the basis of the following criteria:
Circle: No odor, Triangle: Slight odor, Cross: Strong odor
The compositions and evaluation results of the examples are shown in Tables 4 and 5.

Comparative Examples 4 and 5

The Michael addition reaction product (A) produced in Comparative Synthesis Example 1 and Irgacure 907 (2-methyl-1-[4-(methylthio)phenyl]-2-morpholinopropan-1-one: manufactured by Ciba Specialty Chemicals Inc.) were mixed to have compositions shown in Table 5, and evaluated by the same method as in the examples. The results are also shown in Table 5.

TABLE 4

|  | Example 22 | Example 23 | Example 24 | Example 25 |
|---|---|---|---|---|
| Michael addition reaction product 45 | 21 | | | |
| Michael addition reaction product 47 | | 14 | | |
| Michael addition reaction product 59 | | | 20 | |
| Michael addition reaction product 60 | | | | 16 |
| ARONIX M-408 | 20.5 | 27.5 | 21.5 | 25.5 |
| Miramer 4004 | | | | |
| Irg 907 | | | | |
| EAB | 2.5 | 2.5 | 2.5 | 2.5 |
| Vanish | 30 | 30 | 30 | 30 |
| Phthalocyanine blue | 20 | 20 | 20 | 20 |
| Magnesium carbonate | 4 | 4 | 4 | 4 |
| PE wax | 2 | 2 | 2 | 2 |
| Curability | Circle | Circle | Circle | Circle |
| Gloss | 57 | 58 | 55 | 57 |
| Solvent resistance | 25 | 22 | 28 | 27 |
| Cured film odor | Circle | Circle | Circle | Circle |

TABLE 5

| | Example 26 | Comparative Example 4 | Comparative Example 5 |
|---|---|---|---|
| Michael addition reaction product 61 | 24 | | |
| Michael addition reaction product A | | 21 | |
| ARONIX M-408 | 17.5 | 20.5 | 20.5 |
| Miramer 4004 | | | 17.5 |
| Irg 907 | | | 3.5 |
| EAB | 2.5 | 2.5 | 2.5 |
| Vanish | 30 | 30 | 30 |
| Phthalocyanine blue | 20 | 20 | 20 |
| Magnesium carbonate | 4 | 4 | 4 |
| PE wax | 2 | 2 | 2 |
| Curability | Circle | Cross | Circle |
| Gloss | 57 | 51 | 58 |
| Solvent resistance | 20 | 1 | 23 |
| Cured film odor | Circle | Circle | Cross |

<Description of Compounds Shown in Tables>

Michael addition reaction product 45: Michael addition reaction product produced in Example 1

Michael addition reaction product 47: Michael addition reaction product produced in Example 3

Michael addition reaction product 59: Michael addition reaction product produced in Example 5

Michael addition reaction product 60: Michael addition reaction product produced in Example 6

Michael addition reaction product 61: Michael addition reaction product produced in Example 7

Michael addition reaction product A: Michael addition reaction product produced in Comparative Synthesis Example 1

ARONIX M-408: Ditrimethylolpropane tetraacrylate manufactured by Toagosei Co., Ltd.

Miramer 4004: Ethylene oxide-modified pentaerythritol tetraacrylate manufactured by MIWON Co., Ltd.

Irg 907: Photoinitiator, 2-methyl-1-[4-(methylthio)phenyl]-2-morpholinopropan-1-one, manufactured by Ciba Specialty Inc.

EAB: 4,4'-Diethylaminobenzophenone manufactured by Wako Pure Chemical Industries, Ltd.

Phthalocyanine blue: FASTOGEN BLUE TGR-1 manufactured by DIC Corporation

Vanish: 61X1077 Vanish manufactured by DIC Corporation

PE wax: CERIDUST 3615 manufactured by Clariant Inc.

The UV curable ink compositions of the present invention are cured with a practical amount of UV irradiation and are excellent in ink characteristics, and provide ink cured films having little odor. On the other hand, it is obvious that the UV curable ink compositions of the comparative examples are poor in odor or curability.

INDUSTRIAL APPLICABILITY

According to the present invention, an active energy ray-curable composition can be provided, and the composition can be used as a surface coating composition and an ink composition.

The invention claimed is:

1. A Michael addition reaction product obtained by a Michael addition reaction between at least one of compounds represented by general formulae (1) to (5) and (8) and functioning as a Michael donor and at least one of (meth)acrylates having a group functioning as a Michael acceptor, the (meth)acrylates including:

ethyl(meth)acrylate, butyl(meth)acrylate, diethylene di(meth)acrylate, hexanediol di(meth)acrylate, neopentyl glycol di(meth)acrylate, an ethylene oxide-modified product of trimethylolpropane tri(meth)acrylate, pentaerythritol tri(meth)acrylate and an ethylene oxide-modified product of pentaerythritol tri or tetra(meth)acrylate, ditrimethylolpropane tetra(meth)acrylate and an ethylene oxide-modified product thereof, dipentaerythritol tetra, penta, or hexa(meth)acrylate and an ethylene oxide-modified product thereof, an epoxy (meth)acrylate produced by reaction between polyglycidyl ether and (meth)acrylic acid, a urethane(meth)acrylate produced by reaction between a polyisocyanate compound and a hydroxyl group-containing acrylate, a polyester(meth)acrylate produced by reaction between a polybasic acid, a polyol, and a hydroxyl group-containing acrylate, and a high-molecular-weight poly(meth)acrylate produced by reaction between (meth)acrylic acid and a polymer of glycidyl(meth)acrylate and ethyl (meth)acrylate or butyl(meth)acrylate,

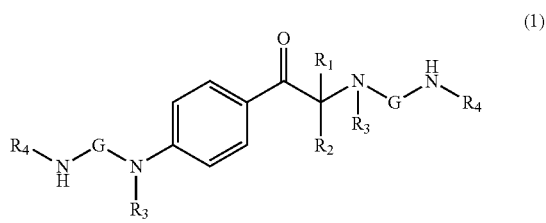

(1)

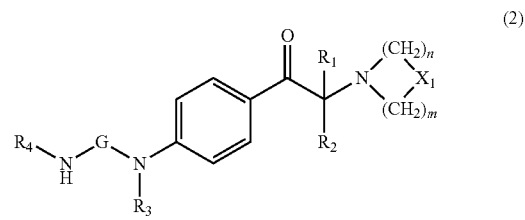

(2)

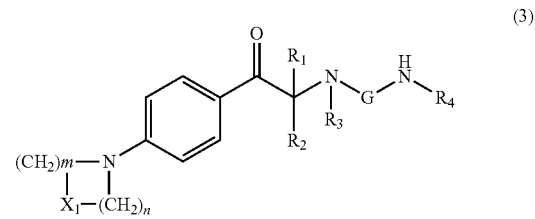

(3)

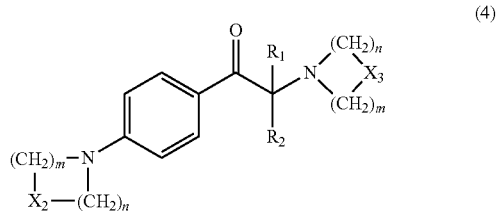

(4)

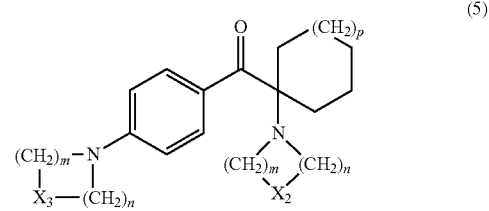

(5)

-continued

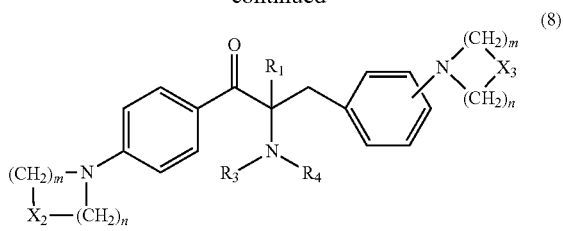

(8)

wherein $R_1$ and $R_2$ each independently represent an alkyl group having 1 to 12 carbon atoms, an allyl group, a cycloalkyl group, an aryl group, or an aralkyl group, G represents an alkylene group having 1 to 12 carbon atoms, a divalent aryl group, or a divalent aralkyl group, $X_1$, $X_2$ and $X_3$ each independently represent NH or O, $R_3$ and $R_4$ each independently represent an alkyl group having 1 to 12 carbon atoms, $R_5$ represents a hydrogen atom, an alkyl group having 1 to 12 carbon atoms, a cycloalkyl group, an aryl group, or an aralkyl group, or a thioalkyl group having 2 to 12 carbon atoms, and m and n each represent 2 or 3, and p represents 0, 1, 2, or 3.

2. The Michael addition reaction product according to claim 1, wherein (number of groups functioning as a Michael donor in at least one of the compounds functioning as a Michael donor/(number of groups functioning as a Michael acceptor in at least one of the (meth)acrylates) is in the range of 1/20 to 1/2, the (meth)acrylates including:

ethyl(meth)acrylate, butyl(meth)acrylate, diethylene di(meth)acrylate, hexanediol di(meth)acrylate, neopentyl glycol di(meth)acrylate, trimethylolpropane tri (meth)acrylate and an ethylene oxide-modified product thereof, pentaerythritol tri or tetra(meth)acrylate and an ethylene oxide-modified product thereof, ditrimethylolpropane tetra(meth)acrylate and an ethylene oxide-modified product thereof, dipentaerythritol tetra, penta, or hexa(meth)acrylate and an ethylene oxide-modified product thereof, an epoxy(meth)acrylate produced by reaction between polyglycidyl ether and (meth)acrylic acid, a urethane (meth)acrylate produced by reaction between a polyisocyanate compound and a hydroxyl group-containing acrylate, a polyester(meth)acrylate produced by reaction between a polybasic acid, a polyol, and a hydroxyl group-containing acrylate, and a high-molecular-weight poly(meth)acrylate produced by reaction between (meth)acrylic acid and a polymer of glycidyl(meth)acrylate and ethyl(meth)acrylate or butyl (meth)acrylate.

3. The Michael addition reaction product according to claim 1, wherein the compounds represented by the general formulae (1) to (5) and (8) and functioning as a Michael donor are compounds represented by general formulae (9) to (19), (10), (13) to (19) below.

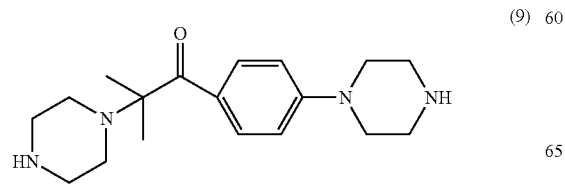

(9)

-continued

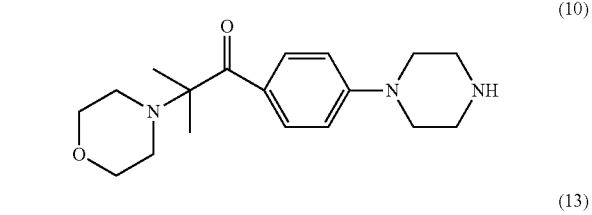

(10)

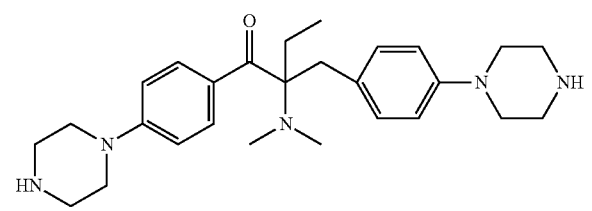

(13)

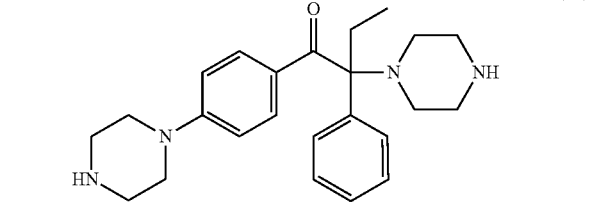

(14)

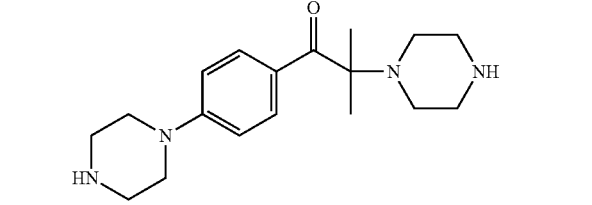

(15)

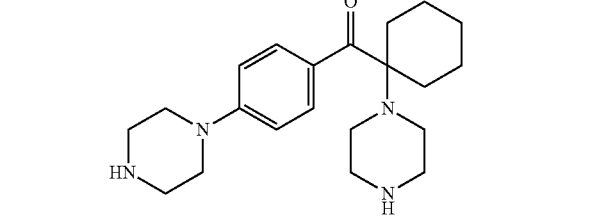

(16)

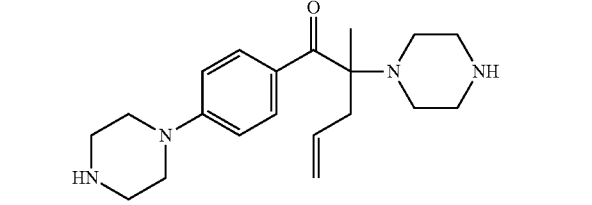

(17)

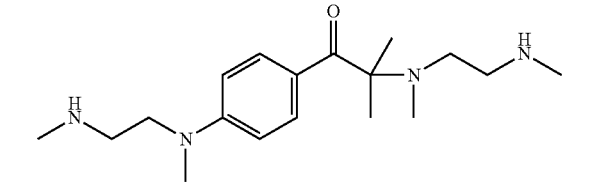

(18)

-continued (19)

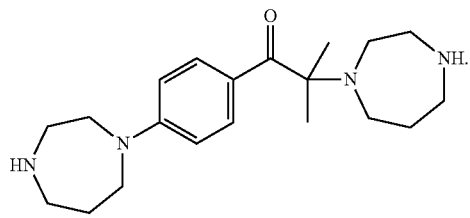

4. A photoinitiator comprising the Michael addition reaction product according to claim 1.

5. A photoinitiator comprising the Michael addition reaction product according to claim 2.

6. A photoinitiator comprising the Michael addition reaction product according to claim 3.

7. An active energy ray-curable composition comprising the photoinitiator according to claim 3.

8. An active energy ray-curable composition comprising the photoinitiator according to claim 5.

9. An active energy ray-curable composition comprising the photoinitiator according to claim 6.

10. An active energy ray-curable ink composition comprising the active energy ray-curable composition according to claim 7.

11. An active energy ray-curable ink composition comprising the active energy ray-curable composition according to claim 8.

12. An active energy ray-curable ink composition comprising the active energy ray-curable composition according to claim 9.

13. An active energy ray-curable surface coating composition comprising the active energy ray-curable composition according to claim 7.

14. An active energy ray-curable surface coating composition comprising the active energy ray-curable composition according to claim 8.

15. An active energy ray-curable surface coating composition comprising the active energy ray-curable composition according to claim 9.

16. The Michael addition reaction product according to claim 2, wherein the compounds represented by the general formulae (1) to (5) and (8) and functioning as a Michael donor are compounds represented by general formulae (9), (10), (13) to (19) below.

(9)

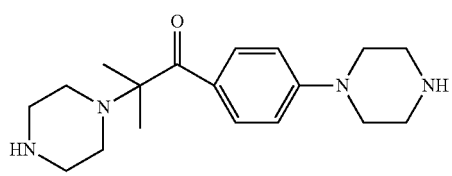

(10)

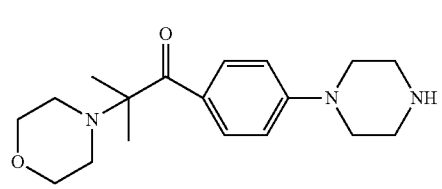

-continued (13)

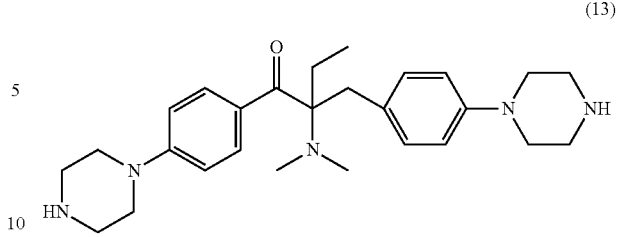

(14)

(15)

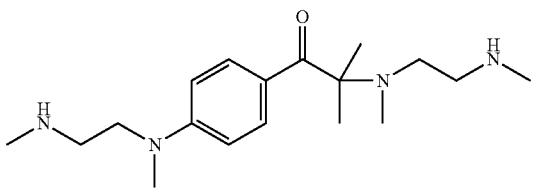

(16)

(17)

(18)

(19)

* * * * *